(12) United States Patent
Xiao et al.

(10) Patent No.: US 9,938,268 B2
(45) Date of Patent: *Apr. 10, 2018

(54) C-RING MODIFIED TRICYCLIC BENZONAPHTHIRIDINONE PROTEIN KINASE INHIBITORS AND USE THEREOF

(75) Inventors: Yufang Xiao, Lexington, MA (US); Bayard R. Huck, Sudbury, MA (US); Amanda E. Sutton, Hingham, MA (US); Thomas E. Richardson, Durham, NC (US); Srinivasa R. Karra, Pembroke, MA (US)

(73) Assignee: Merck Patent GmbH, Darmstadt (DE)

( * ) Notice: Subject to any disclaimer, the term of this patent is extended or adjusted under 35 U.S.C. 154(b) by 12 days.

This patent is subject to a terminal disclaimer.

(21) Appl. No.: 13/140,090

(22) PCT Filed: Dec. 2, 2009

(86) PCT No.: PCT/US2009/066319
§ 371 (c)(1),
(2), (4) Date: Aug. 30, 2011

(87) PCT Pub. No.: WO2010/077530
PCT Pub. Date: Jul. 8, 2010

(65) Prior Publication Data
US 2011/0312951 A1    Dec. 22, 2011

Related U.S. Application Data

(60) Provisional application No. 61/201,961, filed on Dec. 17, 2008.

(51) Int. Cl.
*C07D 471/04* (2006.01)
*C07D 471/14* (2006.01)
*C07D 491/147* (2006.01)
*C07D 495/14* (2006.01)

(52) U.S. Cl.
CPC ......... *C07D 471/04* (2013.01); *C07D 471/14* (2013.01); *C07D 491/147* (2013.01); *C07D 495/14* (2013.01)

(58) Field of Classification Search
CPC ............................ C07D 471/04; C07D 471/14
USPC ............................................. 546/81; 514/290
See application file for complete search history.

(56) References Cited

U.S. PATENT DOCUMENTS

2006/0035920 A1   2/2006 Boyle

FOREIGN PATENT DOCUMENTS

| EP | 459505 A1 | 12/1991 |
|---|---|---|
| JP | 49061198 | * 6/1974 |
| WO | 1997022596 A1 | 6/1997 |
| WO | 1997030035 A1 | 8/1997 |
| WO | 1997032856 A1 | 9/1997 |
| WO | 1998013354 A1 | 4/1998 |
| WO | 1999002166 A1 | 1/1999 |
| WO | 2000040529 A1 | 7/2000 |
| WO | 2000041669 A2 | 7/2000 |
| WO | 2001092224 A1 | 12/2001 |
| WO | 2002004434 A1 | 1/2002 |
| WO | 2002008213 A1 | 1/2002 |
| WO | 2002/044183 A2 | 6/2002 |
| WO | 2004035580 A1 | 4/2004 |
| WO | 2007015837 A2 | 2/2007 |
| WO | 2008016184 A1 | 2/2008 |
| WO | 2008028168 A2 | 3/2008 |
| WO | 2009/108670 | * 9/2009 |

OTHER PUBLICATIONS

Caplus English Abstract DN 125:161858. Lu Zhe Xiong et al 1996.*
Caplus English Abstract DN 125:33447 by Goerlitzer K et al.*
Caplus English abstract JP 49061198, 1974.*
Lücking, et al., ChemMedChem, (2007) 2: 63-77.
Nicolaou, et al., Angewandte Chemie International Edition (2005), 44: 4490-4527.
Dhanabal, et al., Cancer Res. (1999), 59: 189-197.
Xin, et al., J. Biol. Chem. (1999), 274: 9116-9121.
Praveen, Tyle, Pharmaceutical Research (1986), 3(6): 318.
Ditchfield, et al., J. Cell. Biol. (2003), 161: 267-280.
Hauf, et al., J. Cell. Biol. (2003), 161: 281-294.
Emanuel, S., et al., Cancer Res. (2005), 65: 9038-9046.
Kanaoka Yuichi, et al., Heterocycles (1977), 6(1): 29-32.
Mohamed, E. A., et al., Anales de Quimica, Real Sociedad Española de Quimica, Spain (1993), 89(2): 246-253.
Ninomiya, I. et al., Journal of the Chemical Society (Perkin Transactions 1), (1976), 17: 1861-1865.
Ausprunk, et al., Dev. Biol. (1974), 38:237-248.
Berge et al, J. Pharma. Science (1977), 66:1-19.
Gimbrone, et al., J. Natl. Cancer Inst. (1974), 52:413-427.
Nicosia, et al., In Vitro (1982), 18:538549.
Harrington, et al., Nat. Med. (2004), 10:262-267.
Sheu, et al., Anticancer Res. (1998) 18:4435-4441.
K. Goerlitzer and H. J. Ewert, Pharmazie, vol. 51, No. 4, pp. 207-212 (1996).
R. L. Williams and M.G. Elfayoumy, Journal of Heterocyclic Chemistry, vol. 9, No. 5, pp. 1021-1025 (1972).
Nunez, et al., Tetrahedron, 63(29) 6774-6783 (2007).

* cited by examiner

*Primary Examiner* — Rita J Desai

(74) *Attorney, Agent, or Firm* — Thomas W. Brown; EMD Serono Research and Development Institute

(57) ABSTRACT

Disclosed are C-ring modified tricyclic benzonaphthiridinone compounds and analogs thereof, pharmaceutical compositions comprising such compounds and processes for preparing the same. The compounds are useful in the treatment of diseases amenable to protein kinase signal transduction inhibition, regulation and/or modulation.

2 Claims, No Drawings

C-RING MODIFIED TRICYCLIC BENZONAPHTHIRIDINONE PROTEIN KINASE INHIBITORS AND USE THEREOF

FIELD OF THE INVENTION

The present invention relates to protein kinase inhibitors, pharmaceutical compositions comprising such inhibitors, and methods of use thereof.

BACKGROUND OF THE INVENTION

Protein kinases represent a large family of proteins, which play a central role in the regulation of a wide variety of cellular processes, thus maintaining control over cellular function. A partial list of such kinases includes Akt, Axl, Aurora A, Aurora B, Lck, Fyn, Lyn, Yes, dyrk2, epha2, fgfr3, vegfr3, igf1r, IKK2, JNK3, Vegfr2, MEK1, MET, Ron, Rsk1, CHK1, P70s6K, Plk1, RSK1, Src, TrkA, Zap70, cKit, bRaf, EGFR, Jak2, PI3K, NPM-Alk, c-Abl, BTK, FAK, PDGFR, TAK1, LimK, Flt3, Flt1, PDK1 and Erk.

Abnormal cellular responses triggered by protein kinase-mediated events produce a variety of diseases. These include autoimmune diseases, inflammatory diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

Small molecule inhibitors of protein kinases like the Aurora kinases have been reported recently, but their effect on cytokinesis has yet to be investigated in detail. The Aurora family of conserved serine/threonine kinases perform essential functions during cell division. The three mammalian paralogues, Aurora A, B and C, are very similar in sequence, but differ significantly in their localization, function, substrates and regulatory partners. One highly selective and potent small-molecule inhibitor of the Aurora kinases, VX-680, blocks cell-cycle progression and induces apoptosis in a diverse range of human tumor types (Harrington E A, et al., *Natl. J. Med.*, (2004) 10: 262-267). Another novel cell cycle inhibitor, JNJ-7706621, showed potent inhibition of several cyclin-dependent kinases (CDKs) and Aurora kinases, and selectively blocked proliferation of tumor cells of various origins (Emanuel S., et al., *Cancer Res.*, 2005, 65:9038-9046). Additional cellular effects due to inhibition of Aurora kinases included endoreduplication and inhibition of histone H3 phosphorylation.

Aurora kinase inhibitors also have been identified by Hauf et al. (*J. Cell. Biol.*, 2003, 161:281-294), who described the indolinone (Hesperadin) as an inhibitor of Aurora B that causes cells to enter anaphase with monooriented chromosomes; and Ditchfield et al. (*J. Cell. Biol.*, 2003, 161:267-280) who disclosed ZM447439 ((4-(4-(N-benzoylamino)anilino)-6-methoxy-7-(3-(1-morpholino)propoxy)quinazoline), an Aurora kinase inhibitor that interferes with chromosome alignment, segregation, and cytokinesis.

Aprea AB described 9H-carbazole derivatives that inhibit tumor cell growth by disrupting the interaction between the wildtype p53 tumor suppressor gene and HDM2, an oncogene protein, thereby restoring the ability of p53 to induce apoptosis via protein kinase signal transduction (WO 2004/035580 A1).

Takeda Pharmaceuticals Co., Ltd., disclosed pyrido-indole derivatives that are inhibitors of tyrosine kinases and cyclin-dependent kinases, and so are useful as antitumor, antibacterial and anti-viral agents (WO 2008/016184).

However, the need exists for a protein kinase inhibitor that is capable of inhibiting, modulating and/or regulating signal transduction by aberrant protein kinases, thereby effectively treating proliferative diseases such as cancers and cardiovascular, neurodegenerative, inflammatory, and endocrine-related diseases. It is also desirable for this protein kinase inhibitor to be useful in combination therapies for disease treatment and as a diagnostic tool.

These compounds of the present invention and pharmaceutical compositions comprising them are presented either individually or in kit form. Included in this invention also are processes for preparing the compounds that actively modulate or inhibit unregulated protein kinase activity.

Additional objects, features and advantages of the present invention will become apparent to those skilled in the art from the following description and claims.

SUMMARY OF THE INVENTION

The compounds of the invention are selective and highly potent adenosine triphosphate (ATP) competitive inhibitors of Aurora kinases A, B and C, and LimK, Fyn, Lyn, Yes Lck, Src, KDR, Met, Ron, Axl, Flt-3, and FGFR3 protein kinases. The present invention also provides pharmaceutically acceptable derivatives, solvates, salts, tautomers and stereoisomers of these compounds, including mixtures thereof in all ratios. Diseases treated by the use of these novel compounds include primary, secondary, and metastatic cancers such as melanoma, lymphoma, leukemia, colon, colorectal, breast, lung, kidney, pancreatic, renal, CNS, stomach, ovarian, prostate and cervical cancers. Moreover, allergies, asthma, neurodegenerative, endocrine, immunologic, cardiovascular, metabolic, and proliferative diseases all may be treated by use of the compounds of the invention.

In one aspect the invention provides compounds according to Formula I or Formula II:

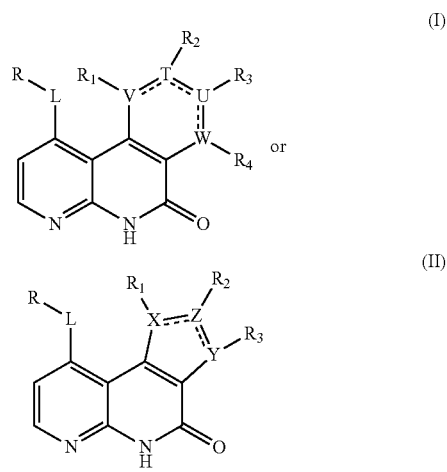

wherein:
T, U, V, W, X, Y, and Z, each independently, is C, CH, N, O or S, depending upon correct valence;
L is NR', O, CR'R', S, or is absent
R is H; halo; CN; $NO_2$; $C_1$-$C_6$ alkyl; $CF_3$; aryl, heteroaryl, aralkyl, alkaryl, heteroalkyl, or carbocycle; C(=O)OR'; alkyl-C(=O)—; —C(=O)aryl; aryl-NH—C(=O)-aryl; aryl-C(=O)—NH-aryl; aryl-NH—C (=O)-heteroaryl; heteroaryl-NH—C(=O)-heteroaryl; heteroaryl-NH—C(=O)-aryl; C(=O)NH-aryl; aryl-C(=O)—; OR'; R'—SO$_2$—; SO$_2$—R'; SR'; R'—NH—C(=O)—; alkyl-O—C(=O)—; R'-alkyl-; R'—C(=O); NR'R'; any of which optionally may be substituted; or is absent.

R' is H; alkyl; haloalkyl; alkylhalo; carbocycle; aryl; heteroaryl, trityl, heteroalkyl, or carboxylic acid ester, any of which may be substituted further;

$R_1$-$R_4$ is H, halo, C—R', NR'R', or OR';

-------- denotes the presence or absence of a double bond;

aryl, heteroaryl or carbocycle optionally may be substituted or unsubstituted, and may be a mono-, bi- or tricyclic ring structure in any combination of aryl, heteroaryl, and/or carbocyclic rings; and a pharmaceutically acceptable prodrug, derivative, solvate, salt, tautomer and stereoisomer thereof, including mixtures thereof in all ratios.

In a preferred embodiment, in the compound according to Formula I not all of T, U, V and W simultaneously are C or CH, depending upon correct valence.

In another preferred embodiment, the compound according to Formula I is incorporated into a pharmaceutical formulation along with one or more pharmaceutically acceptable diluent, excipient, carrier, etc. Those of skill in the art will recognize the overlap in the terms "diluent", "excipient" and "carrier".

Examples of other preferred embodiments of the invention are:

A second preferred embodiment of the present invention comprises a compound in which L is NR', R is a substituted benzamidophenyl moiety, X is CH, Y is N, Z is N, and $R_2$ is H.

A third preferred embodiment of the invention is a compound wherein L is NR', R is a substituted phenylamino moiety, each of T, U, V, and W is CH, and R1-R4 is H.

A fourth preferred embodiment of the invention is a compound in which L is NR'; R is a substituted benzamidophenyl moiety; each of T, V and W is CH, and U is N; $R_1$, $R_2$, and $R_4$ is H; and $R_3$ is benzyl.

Also encompassed by the present invention are methods of treating a subject in need of inhibiting a kinase protein comprising administering to the subject an effective amount of a kinase inhibitor according to Formula I or Formula II In a preferred embodiment, the compound according to Formula I or Formula II is incorporated into a pharmaceutical formulation along with one or more pharmaceutically acceptable diluent, excipient, or carrier, and which further optionally may be packaged as a kit. Provided herein are such pharmaceutical compositions and methods of modulating and/or inhibiting unregulated or disturbed protein kinase activity in order to treat or cure proliferative diseases, including all types of cancers, comprising administering to a subject in need thereof an effective amount of a kinase inhibitor according to Formula I or Formula II.

In a further aspect the invention provides a method for treating or preventing a disease or condition that is a member selected from tumor formation, angiogenesis, arteriosclerosis, ocular diseases, inflammatory diseases, arthritis, and restinosis, among others. The method includes administering to a subject in need thereof a therapeutically effective amount of a compound of Formula I or a pharmaceutically acceptable salt, prodrug, enantiomer, tautomer, hydrate, solvate or racemic mixture thereof. The compounds of Formula I furthermore can be used to provide additive or synergistic effects in certain existing cancer chemotherapies, and/or can be used to restore the efficacy of certain existing cancer chemotherapies and radiotherapies.

Also included within the scope of the invention are compounds 1-51, and a pharmaceutically acceptable salt, prodrug, hydrate, solvate, tautomer, enantiomer or racemic mix of each thereof.

As used herein, the term "solvate" of a compound is meant to comprise solvate of a salt of a compound.

Additional embodiments of the present invention include: a compound according to Formula I or Formula II for use as a medicament; use of the compound according to Formula I or Formula II for the preparation of a medicament for the treatment of a subject in need of inhibiting a kinase protein; and use of the compound according to Formula I or Formula II for the preparation of a medicament for the suppression or reduction of cellular proliferation in single-site or metastatic cancers, or for the inhibition or suppression of cancer metastases.

The present invention also encompasses a compound according to Formula I or Formula II, or a pharmaceutically acceptable derivative, solvate, salt, tautomer and stereoisomer thereof, including mixtures thereof in all ratios, for use in therapy, such as treating a subject in need of modulating or inhibiting a kinase protein, wherein the subject has a proliferative or an inflammatory disease.

Methods of synthesizing the compounds of the present invention also are encompassed within the present invention.

Moreover, the present invention is related to the combined use of a compound of Formula I or Formula II together with further medicament active ingredient for the treatment of a subject in need of treatment for a kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases, autoimmune diseases, cirrhosis, diabetes and vascular and immune diseases in mammals.

BRIEF DESCRIPTION OF THE DRAWINGS

None.

DETAILED DESCRIPTION OF THE INVENTION

The present invention relates to compounds that inhibit, regulate and/or modulate signal transduction by protein kinases, and by Aurora kinases A, B and C, LimK, Fyn, Lyn, Yes, Lyk, Src, KDR, Met, Ron, Axl, Flt-3, and FGFR3 protein kinases in particular. The invention also relates to pharmaceutical compositions that comprise these compounds, and to methods for using the compounds in the treatment of kinase-related diseases and complaints. In a first aspect, the present invention provides a compound having a structure according to Formula I or Formula II:

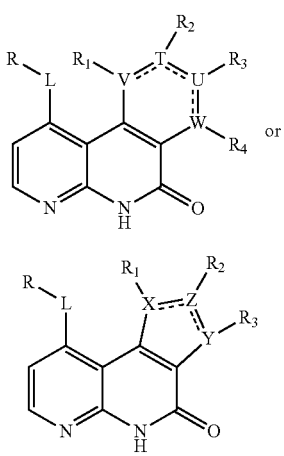

wherein:
T, U, V, W, X, Y, and Z, each independently, is C, CH, N, O or S, depending upon correct valence, with the caveat that not all of T, U, V and W simultaneously are C;
L is NR', O, CR'R', S, or is absent;
R is H; halo; CN; $NO_2$; $C_1$-$C_6$ alkyl; $CF_3$; aryl, heteroaryl, aralkyl, alkaryl, heteroalkyl, or carbocycle; C(=O)OR'; alkyl-C(=O)—; —C(=O)aryl; aryl-NH—C(=O)-aryl; aryl-NH—C(=O)-heteroaryl; heteroaryl-NH—C(=O)-heteroaryl; heteroaryl-NH—C(=O)-aryl; C(=O)NH-aryl; aryl-C(=O)—; OR'; R'—SO$_2$—; SO$_2$—R'; SR'; R'—NH—C(=O)—; alkyl-O—C(=O)—; R'-alkyl-; R'—C(=O); NR'R'; any of which optionally may be substituted; or is absent;
R' is H; alkyl; haloalkyl; alkylhalo; carbocycle; aryl; heteroaryl, trityl, heteroalkyl, or carboxylic acid ester, any of which may be substituted further;
$R_1$-$R_4$ is H, halo, C—R', NR'R', or OR';
-------- denotes the presence or absence of a double bond; aryl, heteroaryl or carbocycle optionally may be substituted or unsubstituted,
and may be a mono-, bi- or tricyclic ring structure in any combination of aryl, heteroaryl, and/or carbocyclic rings; and
a pharmaceutically acceptable prodrug, derivative, solvate, salt, tautomer and stereoisomer thereof, including mixtures thereof in all ratios.
In a preferred embodiment, the compound according to Formula I or Formula II is
incorporated into a pharmaceutical formulation along with one or more pharmaceutically acceptable diluent, excipient, carrier, etc. Those of skill in the art will recognize the overlap in the terms "diluent", "excipient" and "carrier".

The compounds of the present invention are useful for the treatment of a subject in need of inhibition or modulation of a protein kinase, and so are useful in the treatment of inflammatory and/or proliferative disorders.

In a second preferred embodiment of the present invention, L is NR', R is a substituted phenyl moiety, X is CH, Y is N, Z is N, and $R_1$ and $R_2$ each is H.

In a third preferred embodiment, L is NR', R is a substituted phenyl moiety, each of T, U, V and W is $CH_2$, and each of $R_1$-$R_4$ is H.

In a fourth preferred embodiment of the invention, L is NR', R is a substituted phenyl moiety, each of T, V and W is CH, and U is N, each of $R_1$, $R_2$ and $R_4$ is H, $R_3$ is benzyl.

In a fifth preferred embodiment of the invention, L is NR', R is a substituted phenylamino moiety, T, V and W each is $CH_2$, U is N, and each of $R_1$-$R_4$ is H.

In a sixth preferred embodiment of the invention, L is NR', R is a substituted phenylamino moiety, X is O, Y and Z each is C, and $R_2$ and $R_3$ each is H.

In a seventh preferred embodiment of the invention, the compound conforms to formulae (I), (II) or (iii), wherein L is NH and R is aryl-C(=O)—NH-aryl-, wherein each of the aryl moieties can be unsubstituted or independently mono- or disubstituted by halo or $CF_3$.

Yet a further preferred embodiment of the present invention relates to medicaments comprising at least one compound of Formula I or Formula II, and at least one additional medicament active ingredient.

Preferably such medicaments are for the treatment of diseases which are influenced by inhibition of an enzyme selected from the group consisting of Aurora A kinase (EC 2.7.11.1), Aurora B kinase (EC 2.7.11.1), Aurora C kinase (EC 2.7.11.1), Lck (EC 2.7.10.2), Lyn (EC 2.7.10.2), Lim (EC 2.7.11.1), Yes (EC 2.7.10.2), Fyn (EC 2.7.10.2), Src (EC 2.7.10.2), KDR (EC 2.7.10.1), Met (EC 1.1.1.34), Ron (EC 1.1.1.19), Axl (EC 2.7.10.1), Flt-3 (EC 2.7.10.1), and FGFR3 (EC 2.7.10.1). A very preferred medicament according to the invention is for the treatment of diseases which are influenced by modulation or inhibition of the Aurora kinases A, B and/or C.

In a further preferred embodiment the present invention relates to a kit or set comprising separate packs of (a) an effective amount of a compound of the Formula I or Formula II according to the invention, and (b) an effective amount of a further medicament active ingredient.

The compounds of the present invention are useful for the treatment of a subject in need of inhibition or modulation of a protein kinase, and so are useful in the treatment of inflammatory and/or proliferative disorders such as cancers. Thus, also encompassed by the present invention are methods of treating a subject in need of modulating or inhibiting a kinase protein comprising administering to the subject an effective amount of a kinase inhibitor according to Formula I or Formula II. The compounds of Formula I or Formula II furthermore can be used to provide additive or synergistic effects in existing cancer chemotherapies, and/or can be used to restore the efficacy of existing cancer chemotherapies and radiotherapies.

In a preferred embodiment, the compound according to Formula I or Formula II is incorporated into a pharmaceutical formulation along with one or more of a pharmaceutically acceptable diluent, excipient, or carrier, and further optionally may be packaged as a kit.

In a further aspect the invention provides a method for treating or preventing a disease or condition that is a member selected from tumor formation, angiogenesis, arteriosclerosis, ocular diseases, inflammatory diseases, arthritis, and restinosis, among others. The method includes administering to a subject in need thereof a therapeutically effective amount of a compound of Formula I or Formula II or a pharmaceutically acceptable salt, prodrug, enantiomer, tautomer, hydrate, solvate or racemic mixture thereof.

Also included within the scope of the invention are compounds 1-51, and a pharmaceutically acceptable salt, prodrug, hydrate, solvate, tautomer, enantiomer or racemic mix of each thereof.

Additional embodiments of the present invention include: a compound according to Formula I for use as a medicament; use of the compound according to Formula I for the preparation of a medicament for the treatment of a subject in need of inhibiting a kinase protein; and use of the compound according to Formula I or Formula II for the preparation of a medicament for the suppression or reduction of cellular proliferation in single-site or metastatic cancers, or for the inhibition or suppression of cancer metastases.

The present invention also is related to the combined use of a compound of Formula I or Formula II together with further medicament active ingredient for the treatment of a subject in need of treatment for a kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory and hematological diseases, arthritis, thrombosis, fibrosis, glomerulonephritis, neurodegeneration, psoriasis, restenosis, wound healing, transplant rejection, metabolic diseases, autoimmune diseases, cirrhosis, diabetes and vascular and immune diseases in mammals.

II. DEFINITIONS

As used herein, a description of the compounds of the invention in every case includes a pharmaceutically acceptable salt, solvate, hydrate, prodrug, tautomer, enantiomer, stereoisomer, analog or derivative thereof, including mixtures thereof in any ratios.

Where substituent groups are specified by their conventional chemical formulae, written from left to right, they optionally encompass substituents resulting from writing the structure from right to left, e.g., —$CH_2O$— optionally also recites —$OCH_2$—.

The term "alkyl", by itself or as part of another substituent, unless otherwise stated means an unbranched (linear) or branched chain, or a cyclic hydrocarbon radical, or combination thereof, having 1, 2, 3, 4, 5, 6, 7, 8, 9 or 10 C atoms. The term preferably denotes methyl, ethyl, propyl, isopropyl, butyl, isobutyl, sec-butyl or tert-butyl, pentyl, or hexyl, and includes cycloalkyl and bicycloalkyl, e.g. cyclopropyl, cyclobutyl, cyclopentyl, cyclohexyl, cycloheptyl, norbornene, and the like. One to seven hydrogen atoms in an alkyl chain as defined may be replaced by F, Cl and/or Br, and/or one or two CH2 groups may be replaced by O, S, SO, $SO_2$ and/or CH=CH groups.

The terms "haloalkyl" and "alkylhalo" as used herein, respectively, mean a halogen atom such as chlorine, bromine, iodine or fluorine bound to an alkyl group, and in reverse, an alkyl group bound to a halogen atom.

The term "alkylene" denotes an optionally substituted, unbranched (linear) or branched chain that by itself or as part of another substituent means a divalent radical derived from an alkane, as exemplified by —$CH_2CH_2CH_2$—. "Alkylene" preferably denotes methylene, ethylene, propylene, isopropylene, butylene, isobutylene, sec-butylene or tert-butylene, pentylene, 1-, 2- or 3-methylbutylene, 1,1-, 1,2- or 2,2-dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, or difluoromethylene. Especially preferred is an alkylene having 1, 2, 3, 4, 5 or 6 C atoms, preferably methylene, ethylene, propylene, isopropylene, butylene, isobutylene, sec-butylene, tert-butylene, pentylene, hexylene, difluoromethylene, tetrafluoroethylene or 1,1-difluoroethylene.

A "cyclic alkylene" ("cycloalkylene") preferably denotes cyclopropylene, cyclobutylene, cyclopentylene, cyclohexylene or cycloheptylene.

The term "aryl" means, unless otherwise stated, means a polyunsaturated, aromatic, single ring or multiple rings, preferably from 1 to 3 rings, the latter of which are fused together or linked covalently. The term "aryl" denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl including difluorophenyl, o-, m- or p-bromophenyl including dibromophenyl, o-, m- or p-chlorophenyl including dichlorophenyl, o-, m- or p-(methylsulfonamido)phenyl, o-, m- or p-(methylsulfonyl)phenyl, o-, m- or p-methylsulfanylphenyl, o-, m- or p-cyanophenyl, o-, m- or p-carboxyphenyl, o-, m- or p-methoxycarbonylphenyl, o-, m- or p-formylphenyl, o-, m- or p-acetylphenyl, o-, m- or p-aminosulfonylphenyl, o-, m- or p-(morpholin-4-ylcarbonyl)phenyl, o-, m- or p-(morpholin-4-ylcarbonyl)phenyl, o-, m- or p-(3-oxomorpholin-4-yl)phenyl, o-, m- or p-(piperidinylcarbonyl)phenyl, o-, m- or p-[2-(morpholin-4-yl)ethoxy]phenyl, o-, m- or p-[3-(N,N-diethylamino)propoxy]phenyl, o-, m- or p-[3-(3-diethylamino-propyl)ureido]phenyl, o-, m- or p-(3-diethylaminopropoxycarbonylamino)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethyl-aminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl, 5-chloro-benzol[1,3]dioxole, 2-chloro-4-fluoro, or 2,5-dimethyl-4-chlorophenyl.

In a preferred embodiment, "aryl" preferably denotes a phenyl that is unsubstituted or mono-, di- or trisubstituted independently by one or more halogens, OR, CN, $CONH_2$ or a heterocycle, where R is H, alkyl or alkyl chain comprising one or more heteroatoms; or where the substituents join with the carbon atoms of the phenyl to which they are bound to form a second ring, thereby providing a bicyclic structure.

The term "heteroaryl" refers to an aryl ring that contains from one to four heteroatoms selected from N, O, S, Si, P and B, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 7-azaindole, 1-isoquinolyl, 5-isoquinolyl, 2-quinoxalinyl, 5-quinoxalinyl, 3-quinolyl, 6-quinolyl, 1-piperidinyl, 3-benzofuranyl, and 4-benzodioxinyl. Substituents for each of the above noted aryl and heteroaryl ring systems are selected from the group of acceptable substituents described below.

For brevity, the term "aryl" when used in combination with other terms, such as for example, aryloxy, arylthioxy, or arylalkyl, optionally includes both aryl and heteroaryl rings as defined above. Thus, the term "arylalkyl" or "aralkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). This same definition is true in reverse for the term "alkaryl", which includes radicals in which an alkyl group is attached to an aryl group. Each of the terms "alkyl," "heteroalkyl," "aryl" and "heteroaryl" optionally include unsubstituted, mono-, di- or tri-unsubstituted forms of the indicated radical.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

Substituents for the alkyl and heteroalkyl radicals, including those groups often referred to as alkenyl, heteroalkylene, heteroalkenyl, alkynyl, cycloalkyl, heterocycloalkyl, cycloalkenyl, and heterocycloalkenyl, are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, and —$R_1$, wherein $R_1$ is —OH, O-alkyl, —CN, -halo, —C(O)OH, —C(O)O(alkyl), —C(O)$NH_2$, —C(O)NH(alkyl), —C(O)N(alkyl)$_2$, —$CH_2$OH, —$CH_2$O(alkyl), —$CH_2NH_2$, —$CH_2$NH(alkyl), —$CH_2$N(alkyl)$_2$, —$SO_2$OH, —$SO_2$O(alkyl), —$SO_2NH_2$, —$SO_2$NH(alkyl), and —$SO_2$N(alkyl)$_2$. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2$O$CH_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted aryl, substituted or unsubstituted heteroaryl, substituted or unsubstituted heterocycloalkyl, —OH, —O-alkyl, —CN, -halo, —C(O)OH, —C(O)O(alkyl), —C(O)$NH_2$, —C(O)NH(alkyl), —C(O)N(alkyl)$_2$, —$CH_2$OH, —$CH_2$O (alkyl), —$CH_2NH_2$, —$CH_2$NH(alkyl), —$CH_2$N(alkyl)$_2$, —$SO_2$OH, —$SO_2$O(alkyl), —$SO_2NH_2$, —$SO_2$NH(alkyl), and —$SO_2$N(alkyl)$_2$.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes, norbornanes, and the like.

The term "treatment" as used herein refers both to prevention of a particular disease or treatment of a pre-existing condition.

The phrase "therapeutically effective amount" as used herein means that amount of a compound, material, or composition comprising a compound of the present invention which is effective for producing some desired therapeutic effect by simultaneously blocking or inhibiting of protein kinase receptors in a mammal, thereby blocking the biological consequences of that pathway in the treated cells, at a reasonable benefit/risk ratio applicable to any medical treatment.

The term "pharmaceutically acceptable salts" includes salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *J. Pharma. Science* 1977, 66: 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2 hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2 naphthalenesulfonate, nicotinate, nitrate, oxalate, oleate, palmoate, pectinate, persulfate, phenylacetate, 3 phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the Formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as (C1-C4)alkyl halides, for example methyl, ethyl, isopropyl and tert-butyl chloride, bromide and iodide; di(C1-C4)alkyl sulfates, for example dimethyl, diethyl and diamyl sulfate; (C10-C18)alkyl halides, for example decyl, dodecyl, lauryl, myristyl and stearyl chloride, bromide and iodide; and aryl(C1-C4)alkyl halides, for example benzyl chloride and phenethyl bromide. Both water- and oil-soluble compounds according to the invention can be prepared using such salts.

The above-mentioned pharmaceutical salts that are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the Formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As stated, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group that is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

The term "pharmaceutically acceptable salt" as contained herein means an active ingredient which comprises a compound of the Formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention furthermore relates to medicaments comprising at least one compound of the Formula I and/or pharmaceutically usable derivatives, solvates and stereoisomers thereof, including mixtures thereof in all ratios, and optionally excipients and/or adjuvants.

As used herein, the term "prodrug" means a form of the compound that readily undergoes one or more chemical changes under physiological conditions to provide an active form of the compound of the present invention. For instance, typical prodrugs include carboxylic acid ester forms of the compounds of the invention. In an exemplary embodiment, the prodrug is suitable for treatment/prevention of those diseases and conditions that require the drug molecule to cross the blood brain or other membrane bather. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention exist in "unsolvated" forms as well as "solvated" forms, including "hydrated" forms. In general, the solvated forms are equivalent to unsolvated forms, and both are encompassed within the scope of the present invention. Certain compounds of the present invention may exist in multiple crystalline or amorphous forms. In general, all physical forms may be used in the methods contemplated herein and are intended to be within the scope of the present invention. The phrase "a compound or a pharmaceutically acceptable salt, hydrate, polymorph or solvate of a compound" is meant to include both a material that exists in one or more than one of these states.

As used herein, the term "heteroatom" includes oxygen (O), nitrogen (N), sulfur (S), silicon (Si), boron (B), and phosphorus (P).

The term "heteroalkyl," by itself or in combination with another term, unless otherwise stated, means a stable straight or branched chain, cyclic hydrocarbon radical, or combinations thereof, consisting of the stated number of carbon atoms and at least one heteroatom selected from the group consisting of O, N, Si, B, P, and S, wherein the nitrogen and sulfur atoms may optionally be oxidized and the nitrogen heteroatom may optionally be quaternized. The heteroatom(s) O, N, S, B, P, and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group for alkylene and heteroalkylene is implied by the direction in which the formula of the linking group is written. For example, the formula —CO$_2$R'— represents both —C(O)OR' and —OC(O)R'.

The terms "cycloalkyl" or "carbocycle" and "heterocycloalkyl", by themselves or in combination with other terms, unless otherwise stated, mean cyclic versions of "alkyl" and "heteroalkyl", respectively. Additionally, for heterocycloalkyl, a heteroatom occupies any position in the cycle. A "cycloalkyl", "carbocycle" or "heterocycloalkyl" substituent may be attached to the remainder of the molecule directly or through a linker, wherein the linker is, for example, alkyl. Examples of cycloalkyl include, but are not limited to, cyclopentyl, cyclohexyl, 1-cyclohexenyl, 3-cyclohexenyl, cycloheptyl, norbornanyl, norbornene, and the like. The term "carbocycle" as used herein refers to any fully saturated ring structure, including without limitation, cyclopropyl, cyclobutyl, cyclopentyl, cyclohexyl, cycloheptyl, and the like, and also includes mono-, bi- and tri-cyclic forms of the same. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

As used herein, the term "C-ring modified tricyclic benzonaphthiridine" means a third ring added to a benzonaphthiridine scaffold depicted by the following structural arrangement,

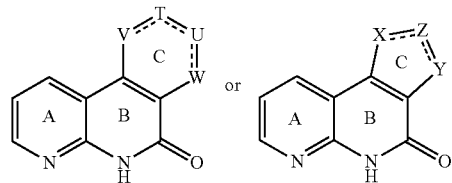

wherein the C ring optionally may be substituted and may vary in size from 4-7 members, of which each member may be a carbon or heteroatom.

Unless otherwise stated, the terms "halo" or "halogen," by themselves or as part of another substituent, mean a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, difluoromethyl, fluoromethyl, 2,2,2-trifluoroethyl, 4-chlorobutyl, 3-bromopropyl, and the like.

Reagents utilized in the syntheses contained herein, unless otherwise noted, have the following meanings: "S-Phos" is 2-dicyclohexylphosphino-2',6'-dimethoxybiphenyl; "Pd(OAc)$_2$" is palladium(II) acetate; "K$_2$CO$_3$" is potassium carbonate; "KOH" is potassium hydroxide; "X-Phos" is 2-dicyclohexylphosphino-2',4',6'-triisopropylbiphenyl; "NaOtBu" is sodium tert-butoxide; and "t-BuOH" is tertiary-butyl hydroxide.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The term "host 'or "patient in need thereof" as used herein may be any mammalian species, for example a primate species, particularly humans; rodents; rabbits; horses, cows, sheep, dogs, cats, etc. Animal models are of interest for veterinary treatment and for experimental investigations, providing a model for treatment of human disease.

By "therapeutically effective amount" of a compound means the amount of the compound that, upon administration, provides the desired beneficial result in a host or patient in need thereof. This amount depends on a number of factors, including, for example, the age and weight of the host, the precise condition that requires treatment and its severity, the nature of the formulation, and the method of administration, and is ultimately determined by the a physician or veterinarian. An effective amount of a compound according to the invention for the treatment of neoplastic growth, for example, is generally in the range from 0.1 to 100 mg/kg/day of body weight of the host recipient. More particularly it is in the range from 1 to 10 mg/kg/day of body weight. Thus, the actual amount per day for an adult mammal weighing 70 kg is usually between 70 and 700 mg, where this amount can be administered as a single dose per day, or may also be administered in a series of partial doses such as, for example, two, three, four, five or six per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

Any drug dosage depends upon the specific compound active agent, the specific disease, patient status, etc. A therapeutic dose typically is considered sufficient at the level at which it reduces the undesired cell population in the target tissue while the viability of the patient is maintained. The treatment is generally continued until a reduction in cell population has occurred, for example, minimally about 50% reduction in cell burden, and may be continued until essentially no more undesired cells are detected in the body.

III. PHARMACEUTICAL COMPOSITIONS, DOSAGES AND ROUTES OF ADMINISTRATION

While compounds of the present invention can be administered as the raw chemical, it
is preferable to present them as a pharmaceutical composition. Thus, one aspect of the present invention provides a pharmaceutical composition comprising a compound of Formula I or a pharmaceutically acceptable salt, hydrate or solvate thereof, together with one or more pharmaceutically acceptable carriers and optionally one or more other therapeutic ingredients. The carrier(s) are "acceptable" in the sense of being compatible with the other ingredients of the formulation and not deleterious to the recipient thereof. The term "pharmaceutically acceptable carrier" includes vehicles, diluents, excipients and other elements appropriate for incorporation into a pharmaceutical formulation.

Pharmaceutical compositions containing compounds of Formula I may be conveniently presented in unit dosage form and prepared by any of the methods well known in the art of pharmacy. Preferred unit dosage formulations are those containing an effective dose, or an appropriate fraction thereof, of the active ingredient, or a pharmaceutically acceptable salt thereof. The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose ranges from about 0.1 mg per day to about 7000 mg per day, preferably about 1 mg per day to about 100 mg per day, and more preferably, about 25 mg per day to about 50 mg per day, in single or divided doses. Preferred dosage unit formulations are those that comprise a daily dose or partial dose, as indicated above, or a corresponding fraction thereof of an active ingredient. Furthermore, pharmaceutical formulations of this type can be prepared using a process that is generally known in the pharmaceutical art. In some embodiments, the total daily dose may range from about 50 mg to about 500 mg per day, and preferably, about 100 mg to about 500 mg per day. Normally it is recommended that children, patients over 65 years old, and those with impaired renal or hepatic function, initially receive low doses and that the dosage is titrated based on individual responses and/or blood levels. It may be necessary to use dosages outside these ranges in some cases, as will be apparent to those in the art. Further, it is noted that the clinician or treating physician knows how and when to interrupt, adjust or terminate therapy in conjunction with individual patient's response.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions. The active ingredient also may be present as a bolus, electuary or paste.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate like starch or mannitol. A flavor, preservative, dispersant and dye may likewise be present.

Capsules are produced by preparing a powder mixture as described above and filling shaped gelatin shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser like agar-agar, calcium carbonate or sodium carbonate, may likewise be added in order to improve the availability of the medicament after the capsule has been taken.

In addition, if desired or necessary, suitable binders, lubricants and disintegrants as well as dyes can be incorporated into the mixture. Suitable binders include starch, gelatin, natural sugars, such as, for example, glucose or beta-lactose, sweeteners made from maize, natural and synthetic rubber like acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted hereto, starch, methylcellulose, agar, bentonite, xanthan gum and the like. Tablets are formulated by preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base as described above, and optionally with a binder, such as carboxymethylcellulose, an alginate, gelatine or polyvinylpyrrolidone, a dissolution retardant, such as, for example, paraffin, an absorption accelerator, such as a quaternary salt, and/or an absorbent like bentonite, kaolin or dicalcium phosphate. The powder mixture can be granulated by wetting it with a binder, such as a syrup, starch paste, acadia mucilage or solutions of cellulose or polymer materials, and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting molds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac-sealing layer, a layer of sugar or polymer material, and a gloss layer of wax may be present. Dyes can be added to these coatings in order to be able to differentiate between different dosage units.

Oral liquids, such as solutions, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of a compound of Formula I in a non-toxic vehicle. Solubilisers and emulsifiers like ethoxylated isostearyl alcohols and polyoxyethylene sorbitol ethers, preservatives, flavor additives, such as peppermint oil, natural sweeteners or saccharin, or other artificial sweeteners and the like, also can be added.

The unit dosage formulations for oral administration, if desired, can be encapsulated in microcapsules. The formulation can also be prepared in such a way that the release is extended or retarded, such as, for example, by coating or embedding of particulate material in polymers, wax and the like.

The compounds of Formula I and salts, solvates and physiologically functional derivatives thereof can also be administered in the form of liposome delivery systems, like small or large unilamellar or multilamellar vesicles, large unilamellar vesicles and multilamellar vesicles. Liposomes can be formed from various phospholipids, such as cholesterol, stearylamine or phosphatidylcholines.

The compounds of Formula I and salts, solvates and physiologically functional derivatives thereof also can be delivered using monoclonal antibodies as individual carriers to which the compound molecules are coupled. The compounds further may be coupled to soluble polymers as targeted medicament carriers. Such polymers encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, (1986) 3(6):318.

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of a formulation to give an ointment, the active ingredient can be employed either with a paraffinic or a water-miscible cream base. Alternatively, the active ingredient can be formulated to give a cream with an oil-in-water cream base or a water-in-oil base. Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered by rapid inhalation via the nasal passages from a container containing the powder held close to the nose. Suitable formulations for administration as nasal spray or nose drops with a liquid as carrier substance encompass solutions of the active-ingredient in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets. Extemporaneous injection solutions and suspensions may be prepared from sterile powders, granules and tablets of the kind previously described. Formulations for rectal administration may be presented as a suppository with the usual carriers such as cocoa butter or polyethylene glycol. Formulations for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The formulations may also comprise other agents usual in the art with respect to the particular type of formulation. Thus, for example, formulations that are suitable for oral administration may comprise flavors.

A formulation of the compound or composition includes any suitable form for parenteral (subcutaneous, intradermal, intramuscular, intravenous, peritoneal and intraarticular), rectal, ionotophoretic, intranasal, inhalation, and oral (including dermal, buccal, sublingual and intraocular) administration. The most suitable route will depend upon the condition and disorder of the recipient. All methods include the step of bringing into association a compound or a pharmaceutically acceptable salt or solvate thereof ("active ingredient") with the pharmaceutically acceptable carrier that constitutes one or more accessory ingredients. In general, the formulations are prepared by uniformly and intimately bringing into association the active ingredient with liquid carriers or finely divided solid carriers or both, and then, if necessary, shaping this formulation into the desired product shape. Oral formulations are well known to those skilled in the art, and general methods for preparing them are found in any standard pharmacy textbook, for example, Remington: *The Science and Practice of Pharmacy*, A. R. Gennaro, ed. (1995), Lippincott.

One aspect of the present invention contemplates the treatment of the disease/condition with the pharmaceutically active agent that may be sold in kit form. The kit comprises a compound of the present invention contained within a syringe, box, bag, and the like. Typically, the kit comprises directions for the administration of the compound. The kit form is particularly advantageous when different dosage concentrations and/or forms (e.g., oral and parenteral) are sold, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). They generally consist of a sheet of relatively stiff material covered with a foil of a preferably transparent plastic material. During the packaging process recesses are formed in the plastic foil. The recesses have the size and shape of the tablets or capsules to be packed. The tablets or capsules are placed in the recesses and the sheet of relatively stiff material is sealed against the plastic foil at the face of the foil which is opposite from the direction in which the recesses were formed. Particular dosage information normally is stamped onto each blister pack.

In another specific embodiment of the invention, a dispenser designed to dispense the daily doses one at a time in the order of their intended use is provided.

IV. METHODS OF TREATMENT OR PREVENTION

In a further aspect the invention provides a method for treating or preventing a disease or condition that is a member selected from kinase-related malfunction, and especially for diseases such as angiogenesis, cancers, tumor formation, growth and propagation, arteriosclerosis, ocular diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic diseases, autoimmune diseases, haematological diseases, cirrhosis, diabetes and vascular and immune diseases in mammals. The method includes administering to a subject in need thereof a therapeutically effective amount of a compound of Formula I or a pharmaceutically acceptable salt, hydrate, prodrug, tautomer, enantiomer, or racemic mix thereof:

Subjects for treatment according to the present invention include humans (patients) and other mammals in need of therapy for the stated condition.

Compounds of the invention possess unique pharmacological characteristics with respect to inhibition of cellular division and influence the activity of the Aurora kinase enzymes in cells. Therefore, these compounds are effective in treating conditions and disorders, especially cancer-related tumors and disorders, which are modulated by Aurora kinase activity. In one embodiment, compounds of the invention are associated with diminished side effects compared to other current standards of treatment.

Compounds of the invention are typically more selective than known anti-cancer drugs, and demonstrate higher selectivity for inhibiting certain protein kinase activity. The compounds also exhibit an advantageous profile of activity including good bioavailability. Accordingly, they offer advantages over many art-known methods for treating disorders associated with unregulated or disturbed protein kinase activity.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents, for example, cis-platin, carboplatin, cyclophosphamide, nitrogen mustard, melphalan, chlorambucil, busulphan and nitrosoureas; antimetabolites, for example, antifolates such as fluoropyrimidines like 5-fluorouracil and tegafur, raltitrexed, methotrexate, cytosine arabinoside, hydroxyurea and gemcitabine; antitumour antibiotics, for example, anthracyclines, like adriamycin, bleomycin, doxorubicin, daunomycin, epirubicin, idarubicin, mitomycin-C, dactinomycin and mithramycin; antimitotic agents, for example, vinca alkaloids, like vincristine, vinblastine, vindesine and vinorelbine, and taxoids, like taxol and taxotere; topoisomerase inhibitors, for example, epipodophyllotoxins, like etoposide and teniposide, amsacrine, topotecan, irinotecan and camptothecin; and cell-differentiating agents, for example, all-trans-retinoic acid, 13-cis-retinoic acid and fenretinide;

(ii) cytostatic agents, such as antioestrogens, for example, tamoxifen, toremifene, raloxifene, droloxifene and iodoxyfene, oestrogen receptor downregulators, for example, fulvestrant; antiandrogens, for example, bicalutamide, flutamide, nilutamide and cyproterone acetate; LHRH antagonists or LHRH agonists, for example, goserelin, leuprorelin and buserelin; progesterones, for example, megestrol acetate; aromatase inhibitors, for example, as anastrozole, letrozole, vorazole and exemestane; and inhibitors of 5'-reductase, such as finasteride;

(iii) agents which inhibit cancer cell invasion, for example, metalloproteinase inhibitors, like marimastat, and inhibitors of urokinase plasminogen activator receptor function;

(iv) inhibitors of growth factor function, for example, such inhibitors include growth factor antibodies, growth factor receptor antibodies, for example, the anti-erbb2 antibody trastuzumab [Herceptin™] and the anti-erbb1 antibody cetuximab [C225], farnesyl transferase inhibitors, serine/threonine kinase inhibitors and serine/threonine kinase inhibitors, for example, inhibitors of the epidermal growth factor family, for example, EGFR family serine/threonine kinase inhibitors, such as N (3-chloro-4-fluorophenyl)-7-methoxy-6-(3-morpholinopropoxy) quinazolin-4-amine (gefitinib, AZD1839), N (3-ethynylphenyl)-6,7 bis(2-methoxyethoxy)quinazolin-4-amine (erlotinib, OSI-774) and 6 acrylamido-N-(3-chloro-4-fluorophenyl)-7-(3-morpholinopropoxy)quinazolin-4-amine (CI 1033); inhibitors of the platelet-derived growth factor family; and inhibitors of the hepatocyte growth factor family;

(v) antiangiogenic agents, such as those which inhibit the effects of vascular endothelial growth factor, for example, the anti-vascular endothelial cell growth factor antibody bevacizumab [Avastin™]; compounds such as those disclosed in published international patent applications WO 97/22596, WO 97/30035, WO 97/32856 and WO 98/13354) and compounds that work by other mechanisms, (for example, linomide, inhibitors of integrin function and angiostatin;

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example, those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT; gene-directed enzyme pro-drug therapy approaches, such as those using cytosine deaminase, thymidine kinase or a bacterial nitroreductase enzyme; and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines like interleukin 2, interleukin 4 or granulocyte-macrophage colony stimulating factor; approaches for decreasing T cell anergy; approaches using transfected immune cells, such as cytokine-transfected dendritic cells; approaches using cytokine-transfected tumour cell lines; and approaches using anti-idiotypic antibodies.

The medicaments from Table 1 below are preferably, but not exclusively, combined with the compounds of the Formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | Chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 |
| | Ormiplatin | (Hoffmann-La Roche) |
| | Iproplatin | SM-11355 (Sumitomo) |
| | | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | |
| | Teniposide or mitoxantrone | Quinamed (ChemGenex) |
| | | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | | BNP-1350 (BioNumerik) |

TABLE 1-continued

| Category | | |
|---|---|---|
| | Pixantrone (Novuspharrna) | CKD-602 (Chong Kun Dang) |
| | Rebeccamycin analogue (Exelixis) | KW-2170 (Kyowa Hakko) |
| | BBR-3576 (Novuspharrna) | |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | | Bleomycin sulfate (Blenoxan) |
| | Epirubicin | Bleomycinic acid |
| | Therarubicin | Bleomycin A |
| | Idarubicin | Bleomycin B |
| | Rubidazone | Mitomycin C |
| | Plicamycinp | MEN-10755 (Menarini) |
| | Porfiromycin | GPX-100 (Gem Pharmaceuticals) |
| | Cyanomorpholinodoxo-rubicin | |
| | Mitoxantron (Novantron) | |
| Antimitotic agents | Paclitaxel | SB 408075 (GlaxoSmithKline) |
| | Docetaxel | E7010 (Abbott) |
| | Colchicine | |
| | Vinblastine | PG-TXL (Cell Therapeutics) |
| | Vincristine | |
| | Vinorelbine | IDN 5109 (Bayer) |
| | Vindesine | A 105972 (Abbott) |
| | Dolastatin 10 (NCI) | A 204197 (Abbott) |
| | Rhizoxin (Fujisawa) | LU 223651 (BASF) |
| | Mivobulin (Warner-Lambert) | D 24851 (ASTA Medica) |
| | | ER-86526 (Eisai) |
| | Cemadotin (BASF) | Combretastatin A4 (BMS) |
| | RPR 109881A (Aventis) | Isohomohalichondrin-B (PharmaMar) |
| | TXD 258 (Aventis) | |
| | Epothilone B (Novartis) | ZD 6126 (AstraZeneca) |
| | T 900607 (Tularik) | PEG-Paclitaxel (Enzon) |
| | T 138067 (Tularik) | AZ10992 (Asahi) |
| | Cryptophycin 52 (Eli Lilly) | IDN-5109 (Indena) |
| | Vinflunine (Fabre) | AVLB (Prescient NeuroPharma) |
| | Auristatin PE (Teikoku Hormone) | Azaepothilone B (BMS) |
| | BMS 247550 (BMS) | BNP-7787 (BioNumerik) |
| | BMS 184476 (BMS) | CA-4-Prodrug (OXiGENE) |
| | BMS 188797 (BMS) | Dolastatin-10 (NrH) |
| | Taxoprexin (Protarga) | CA-4 (OXiGENE) |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-Benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | lonafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | |
| | MS-209 (Schering AG) | Biricodar dicitrate (Vertex) |
| Histone acetyl transferase inhibitors | Tacedinaline (Pfizer) | Pivaloyloxymethyl butyrate (Titan) |
| | SAHA (Aton Pharma) | |
| | MS-275 (Schering AG) | Depsipeptide (Fujisawa) |
| Metalloproteinase inhibitors | Neovastat (Aeterna Laboratories) | CMT-3 (CollaGenex) |
| | | BMS-275291 (Celltech) |
| Ribonucleoside reductase inhibitors | Marimastat (British Biotech) | Tezacitabine (Aventis) |
| | Gallium maltolate (Titan) | Didox (Molecules for Health) |
| | Triapin (Vion) | |
| TNF-alpha agonists/ antagonists | Virulizin (Lorus Therapeutics) | Revimid (Celgene) |
| | CDC-394 (Celgene) | |

TABLE 1-continued

| | | |
|---|---|---|
| Endothelin-A receptor antagonists | Atrasentan (Abbot)<br>ZD-4054 (AstraZeneca) | YM-598 (Yamanouchi) |
| Retinoic acid receptor agonists | Fenretinide (Johnson & Johnson)<br>LGD-1550 (Ligand) | Alitretinoin (Ligand) |
| Immunomodulators | Interferon<br>Oncophage (Antigenics)<br>GMK (Progenics)<br>Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (GemVax) | Dexosome therapy (Anosys)<br>Pentrix (Australian Cancer Technology)<br>JSF-154 (Tragen)<br>Cancer vaccine (Intercell)<br>Norelin (Biostar)<br>BLP-25 (Biomira)<br>MGV (Progenics)<br>3-Alethin (Dovetail)<br>CLL-Thera (Vasogen) |
| Hormonal and antihormonal agents | Oestrogens<br>Conjugated oestrogens<br>Ethynyloestradiol<br>chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin |
| Tyrosine kinase inhibitors | Imatinib (Novartis)<br>Leflunomide(Sugen/Pharmacia)<br>ZD1839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmithKline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic)<br>GCS-IOO (gal3 antagonist, GlycoGenesys)<br>G17DT immunogen (gastrin inhibitor, Aphton)<br>Efaproxiral (oxygenator, Allos Therapeutics)<br>PI-88 (heparanase inhibitor, Progen)<br>Tesmilifen (histamine antagonist, YM BioSciences)<br>Histamine (histamine H2 receptor agonist, Maxim) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore)<br>3CPA (NF-kappaB inhibitor, Active Biotech)<br>Seocalcitol (vitamin D receptor agonist, Leo)<br>131-I-TM-601 (DNA antagonist, TransMolecular)<br>Eflornithin (ODC inhibitor, ILEX Oncology)<br>Minodronic acid (osteoclast inhibitor, Yamanouchi) |

TABLE 1-continued

| | |
|---|---|
| Tiazofurin (IMPDH inhibitor, Ribapharm) | Indisulam (p53 stimulant, Eisai) |
| Cilengitide (integrin antagonist, Merck KGaA) | Aplidin (PPT inhibitor, PharmaMar) |
| SR-31747 (IL-1 antagonist, Sanofi-Synthelabo) | Rituximab (CD20 antibody, Genentech) |
| CCI-779 (mTOR kinase inhibitor, Wyeth) | Gemtuzumab (CD33 antibody, Wyeth Ayerst) |
| Exisulind (PDE-V inhibitor, Cell Pathways) | PG2 (haematopoiesis promoter, Pharmagenesis) |
| CP-461 (PDE-V inhibitor, Cell Pathways) | Immunol ™ (triclosan mouthwash, Endo) |
| AG-2037 (GART inhibitor, Pfizer) | Triacetyluridine (uridine prodrug, Wellstat) |
| WX-UK1 (plasminogen activator inhibitor, Wilex) | SN-4071 (sarcoma agent, Signature BioScience) |
| PBI-1402 (PMN stimulant, ProMetic LifeSciences) | TransMID-107 ™ (immunotoxin, KS Biomedix) |
| Bortezomib (proteasome inhibitor, Millennium) | PCK-3145 (apoptosis promoter, Procyon) |
| SRL-172 (T-cell stimulant, SR Pharma) | Doranidazole (apoptosis promoter, Pola) |
| TLK-286 (glutathione-S transferase inhibitor, Telik) | CHS-828 (cytotoxic agent, Leo) |
| PT-100 (growth factor agonist, Point Therapeutics) | Trans-retinoic acid (differentiator, NIH) |
| Midostaurin (PKC inhibitor, Novartis) | MX6 (apoptosis promoter, MAXIA) |
| Bryostatin-1 (PKC stimulant, GPC Biotech) | Apomine (apoptosis promoter, ILEX Oncology) |
| CDA-II (apoptosis promoter, Everlife) | Urocidin (apoptosis promoter, Bioniche) |
| SDX-101 (apoptosis promoter, Salmedix) | Ro-31-7453 (apoptosis promoter, La Roche) |
| Ceflatonin (apoptosis promoter, ChemGenex) | Brostallicin (apoptosis promoter, Pharmacia) |

A combined treatment of this type can be achieved with the aid of simultaneous, consecutive or separate dispensing of the individual components of the treatment. Combination products of this type employ the compounds according to the invention.

V. GENERAL SYNTHESES

The compounds of the invention are prepared in general by methods known to those of skill in the art for synthesizing analogous compounds. These are illustrated by the general schemes indicated below, and the preparative examples that follow. Most starting materials are commercially available from supply companies like Aldrich Chemicals Co. or Sigma Chemical Company, as examples. Compounds that are not commercially available may be synthesized by those of skill in the art by following procedures given in references such as "*Organic Reactions*," Volumes 1-40, John Wiley & Sons (1991); "*Rodd's Chemistry of Carbon Compounds*," Volumes 1-5 and Suppl., Elservier Science Publishers (1989); "*Fieser and Fieser's Reagents for Organic Synthesis*," Volume 1-15, John Wiley & Sons (1991); "*Advanced Organic Chemistry*," Jerry March, John Wiley & Sons, 4$^{th}$ Ed. (1992); Lücking et al, *ChemMedChem* 2007, 2, 63-77; and Nicolaou. et al. *Agew. Chem. Int. Ed.* 2005, 44, 4490-4527. All compounds of the present invention were synthesized by processes developed by the inventors.

The following schemes depict general syntheses for the compounds of the present invention.

SCHEME 1

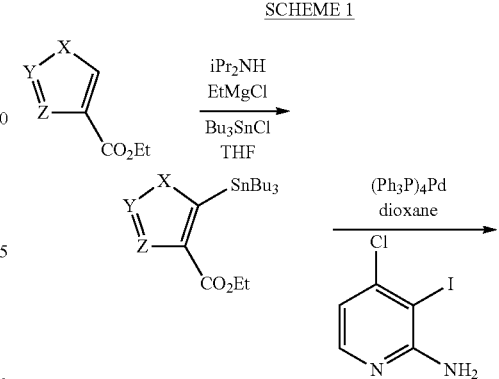

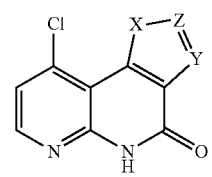

SCHEME 2
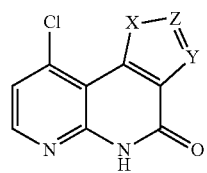 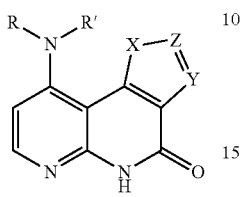
SCHEME 5
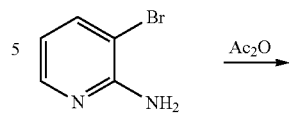
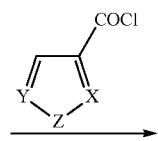
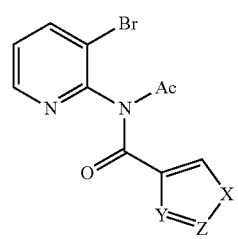
SCHEME 3
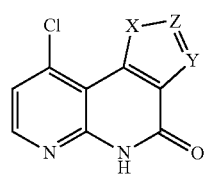 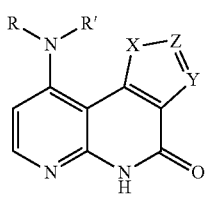
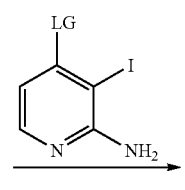
SCHEME 4
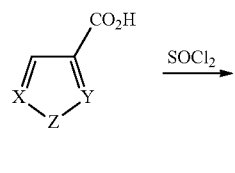 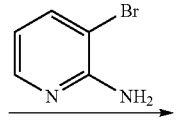 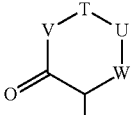
SCHEME 6
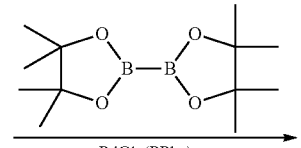
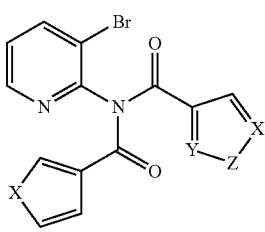
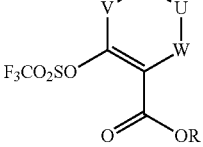
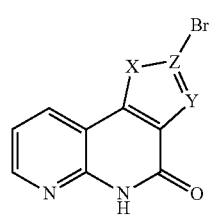 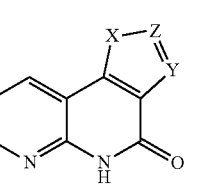
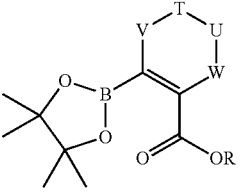

VI. EXAMPLES

Example 1 (Intermediate)

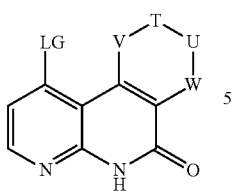

2-Trifluoromethanesulfonyloxy-cyclohex-1-enecarboxylic acid ethyl (1)

To a suspension of sodium hydride (1.35 g, 33.9 mmol) in diethyl ether (150 mL) was added dropwise a solution of ethyl 2-oxocyclohexanecarboxylate (5.00 g, 29.4 mmol) diethyl ether (30 mL). After stirring for 2 h at room temperature, trifluoromethanesulfonic anhydride (5.7 mL, 33.8 mmol) was added dropwise, and the reaction mixture was stirred for 16 h at room temperature. The reaction was quenched with saturated ammonium chloride (200 mL), and the product was extracted with ether (3×100 mL). The combined ether extracts were dried over MgSO$_4$, filtered, and concentrated to provide compound (1), which was used in the next step without further purification.

Example 2 (Intermediate)

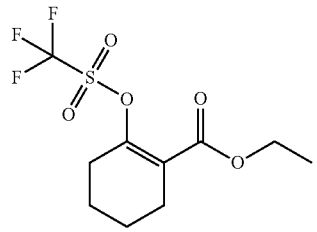 [SMILES: CCOC(=O)C1=C(OS(=O)(=O)C(F)(F)F)CCCC1]

Ethyl 2-(4,4,5,5-tetramethyl-1,3,2-dioxaborolan-2-yl)cyclohex-1-ene-1-carboxylate (2)

The compound of Example (1) (6.50 g, 21.5 mmol), 4,4,4',4',5,5,5',5'-octamethyl-2,2'-bi-1,3,2-dioxaborolane (6.01 g, 23.6 mmol), dichloro[bis(triphenylphosphoranyl)] palladium (1.51 g, 2.1 mmol), triphenylphosphine (1.13 g, 4.3 mmol), and K$_2$CO$_3$ (5.94 g, 43.0 mmol) were suspended in dioxane, and stirred overnight at 100° C. After cooling to room temperature, the reaction was concentrated, ether and water were added and the mixture was extracted with ether. The combined ether extracts were washed with brine, dried over MgSO$_4$, filtered and concentrated. The crude product was purified via silica gel chromatography to provide compound (2) (1.8 g, 16% yield—two steps) as a colorless oil. LC-MS (M+H=281, obsd.=281). $^1$H NMR (400 MHz, d6-DMSO): δ 1.32 (t, J=3.6 Hz, 3H), 1.33 (s, 12H), 1.55 (m, 4H), 2.20 (m, 4H), 4.18 (q, J=3.6 Hz, 2H).

-continued

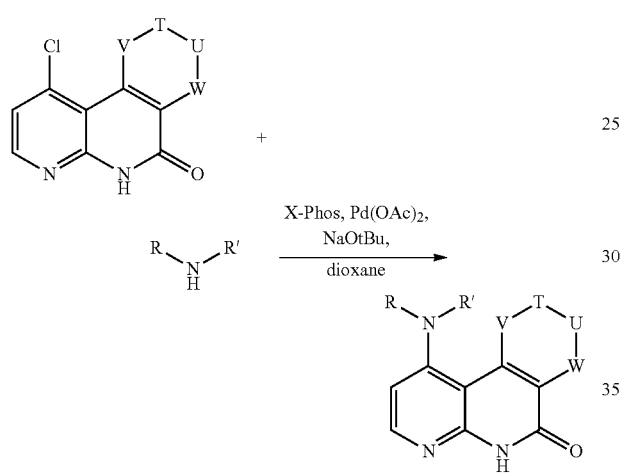

SCHEME 7

SCHEME 8

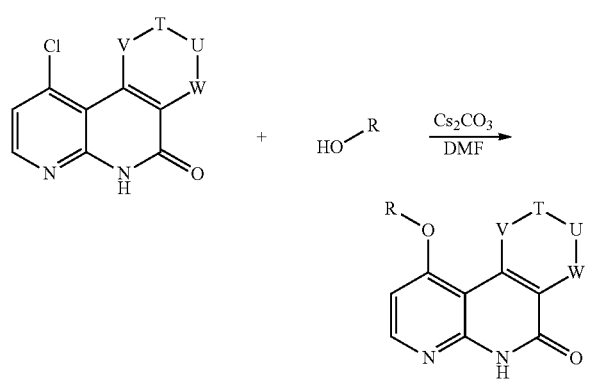

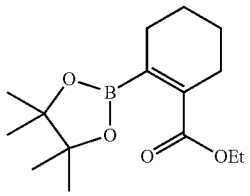 [SMILES: CCOC(=O)C1=C(B2OC(C)(C)C(C)(C)O2)CCCC1]

Example 3

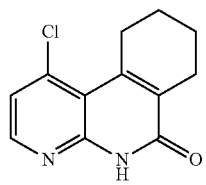 [SMILES: O=c1[nH]c2nccc(Cl)c2c2c1CCCC2]

1-Chloro-7,8,9,10-tetrahydro-5H-benzo[c][1,8]naphthyridin-6-one (3)

4-Chloro-3-iodopyridin-2-amine (1.40 g, 5.50 mmol), 2 (1.70 g; 6.05 mmol), Pd(OAc)₂ (0.12 g, 0.55 mmol), S-Phos (0.45 g, 1.10 mmol), and K₂CO₃ (1.52 g, 11.00 mmol) were suspended in dioxane/water (8 mL/1 mL), and stirred overnight at 100° C. After cooling to room temperature, the mixture was poured in ice water. The resulting precipitate was filtered, washed with water and EtOAc, and dried under vacuum to provide compound (3) (600 mg, 46% yield). LC-MS (M+H=235, obsd.=235). ¹H NMR (400 MHz, d6-DMSO): δ 1.70 (m, 4H), 3.18 (m, 2H), 3.65 (m, 2H), 7.32 (d, J=7.6 Hz, 1H), 8.31 (d, J=7.6 Hz, 1H).

Example 4

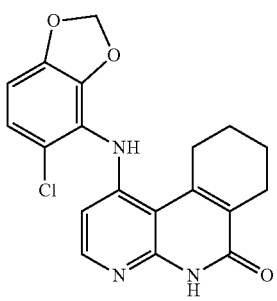 [SMILES: O=c1[nH]c2nccc(Nc3c(Cl)ccc4c3OCO4)c2c2c1CCCC2]

1-(5-Chloro-benzo[1,3]dioxol-4-ylamino)-7,8,9,10-tetrahydro-5H-benzo[c][1,8]naphthyridin-6-one (4)

The compound of Example 3 (100 mg, 0.37 mmol), 5-chloro-benzo[1,3]dioxol-4-ylamine (95 mg, 0.55 mmol), Pd(OAc)₂ (4 mg, 0.02 mmol), X-Phos (18 mg, 0.04 mmol), and NaOtBu (106 mg, 1.11 mmol) were suspended in dioxane (2.0 mL), and stirred overnight at 100° C. The reaction mixture was diluted with EtOAc/H₂O. The resulting precipitate was filtered, washed with EtOAc, and dried under vacuum to provide 4 (19 mg, 14% yield) as a tan solid. LC-MS (M+H=370, obsd.=370).

Example 5

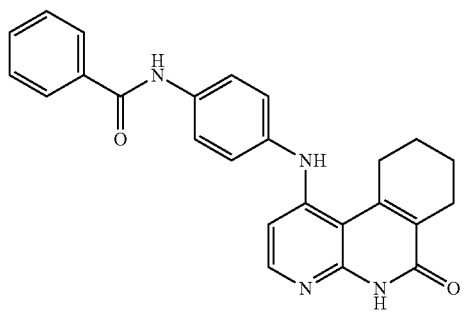 [SMILES: O=C(Nc1ccc(Nc2ccnc3[nH]c(=O)c4c(c23)CCCC4)cc1)c1ccccc1]

N-[4-(6-Oxo-5,6,7,8,9,10-hexahydrobenzo[c][1,8] naphthyridin-1-ylamino)-phenyl]-benzamide (5)

The compound of Example (3) (150.0 mg, 0.64 mmol) was suspended in ether (5 mL) and HCl (1.28 mL in ether; 1.00 M; 1.28 mmol), and the mixture was stirred for 2 h at room temperature. The reaction mixture was concentrated, and resuspended in NMP (2 mL). N-(4-aminophenyl)benzamide (163 mg, 0.77 mmol) was added, and the reaction mixture was stirred for 3 h at 150° C. After cooling to room temperature, water was added. The resulting precipitate was filtered, washed with water and MeOH, and dried under vacuum to provide compound (5) (70 mg, 27% yield). LC-MS (M+H=411, obsd.=411). ¹H NMR (400 MHz, d6-DMSO): δ 1.70 (m, 4H), 1.64 (m, 2H), 1.71 (m, 2H), 2.67 (m, 2H), 3.13 (m, 2H), 6.81 (m, 1H), 7.1879 (m, 1H), 7.74 (m, 2H), 7.76 (m, 1H), 7.97 (m, 1H), 8.03 (m, 1H), 10.25 (s, 1H), 11.67 (s, 1H).

Example 6

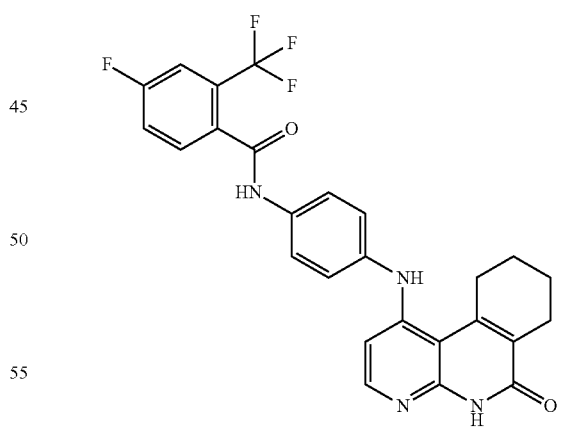

4-Fluoro-N-[4-(6-oxo-5,6,7,8,9,10-hexahydrobenzo [c][1,8]naphthyridin-1-ylamino)-phenyl]-2-trifluoromethyl-1-benzamide (6)

The title compound was synthesized according to the procedure described for the preparation of Example 5. LC-MS (M+H=497, obsd.=497). ¹H NMR (400 MHz, d6-DMSO): δ 1.67 (m, 2H), 1.73 (m, 2H), 2.50 (m, 2H), 3.19 (m, 2H), 6.77 (m, 1H), 7.28 (m, 2H), 7.73 (m, 2H), 7.78 (m, 2H), 8.04 (m, 1H), 8.58 (s, 1H), 10.64 (s, 1H).

Example 7

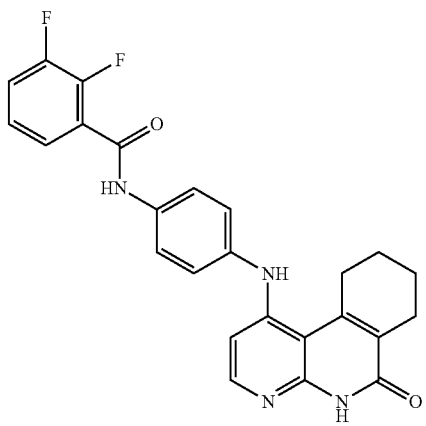 [SMILES: O=C(Nc1ccc(Nc2ccnc3[nH]c(=O)c4c(c23)CCCC4)cc1)c1cccc(F)c1F]

2,3-Difluoro-N-[4-(6-oxo-5,6,7,8,9,10-hexahydrobenzo[c][1,8]naphthyridin-1-ylamino)-phenyl]-1-benzamide (7)

The title compound was synthesized according to the procedure described for the preparation of Example 5. LC-MS (M+H=447, obsd.=447). ¹H NMR (400 MHz, d6-DMSO): δ 1.68 (m, 2H), 1.73 (m, 2H), 2.51 (m, 2H), 3.20 (m, 2H), 6.77 (d, J=8.1 Hz, 2H), 7.27 (d, J=8.1 Hz, 2H), 7.32 (m, 1H), 7.49 (m, 1H), 7.64 (m, 1H), 7.78 (d, J=8.0 Hz, 2H), 8.03 (d, J=8.0 Hz, 2H), 8.59 (s, 1H), 10.63 (s, 1H).

Example 8

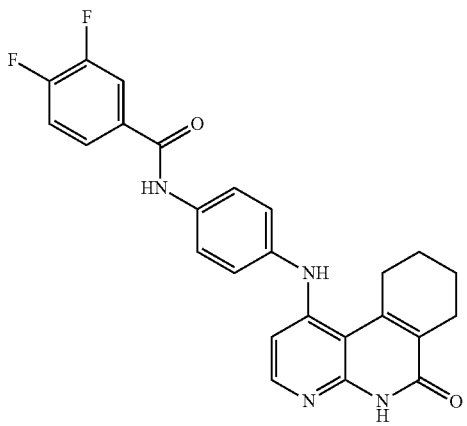 [SMILES: O=C(Nc1ccc(Nc2ccnc3[nH]c(=O)c4c(c23)CCCC4)cc1)c1ccc(F)c(F)c1]

3,4-Difluoro-N-[4-(6-oxo-5,6,7,8,9,10-hexahydrobenzo[c][1,8]naphthyridin-1-ylamino)-phenyl]-1-benzamide (8)

The title compound was synthesized according to the procedure described for the preparation of Example 5. LC-MS (M+H=447, obsd.=447). ¹H NMR (400 MHz, d6-DMSO): δ 1.67 (m, 2H), 1.73 (m, 2H), 2.53 (m, 2H), 3.20 (m, 2H), 6.77 (m, 1H), 7.28 (m, 2H), 7.64 (m, 1H), 7.82 (m, 1H), 7.91 (m, 1H), 8.06 (m, 2H), 8.68 (s, 1H), 10.41 (s, 1H).

Example 9

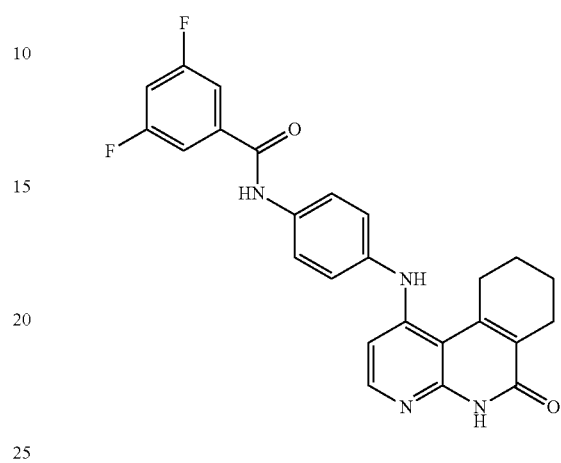

3,5-Difluoro-N-[4-(6-oxo-5,6,7,8,9,10-hexahydrobenzo[c][1,8]naphthyridin-1-ylamino)-phenyl]-1-benzamide (9)

The title compound was synthesized according to the procedure described for the preparation of Example 5. LC-MS LC-MS (M+H=447, obsd.=447). ¹H NMR (400 MHz, d6-DMSO): δ 1.67 (m, 2H), 1.74 (m, 2H), 2.51 (m, 2H), 3.19 (m, 2H), 6.77 (m, 1H), 7.28 (m, 2H), 7.54 (m, 1H), 7.71 (m, 1H), 7.79 (m, 1H), 8.05 (m, 2H), 8.59 (s, 1H), 10.44 (s, 1H).

Example 10

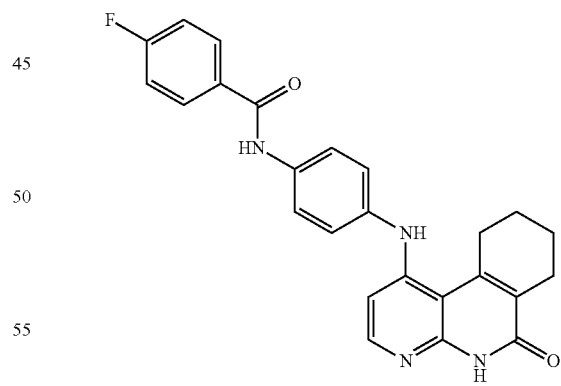

4-Fluoro-N-[4-(6-oxo-5,6,7,8,9,10-hexahydrobenzo[c][1,8]naphthyridin-1-ylamino)-phenyl]-1-benzamide (10)

The title compound was synthesized according to the procedure described for the preparation of Example 5. LC-MS (M+H=429, obsd.=429). ¹H NMR (400 MHz, d6-DMSO): δ 1.66 (m, 2H), 1.73 (m, 2H), 2.53 (m, 2H), 3.19 (m, 2H), 6.77 (m, 1H), 7.32 (m, 2H), 7.41 (m, 2H), 7.81 (m, 2H), 8.05 (m, 2H), 8.68 (s, 1H), 10.35 (s, 1H).

Example 11

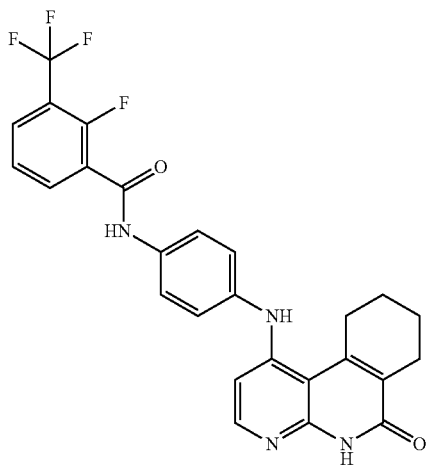 [SMILES: O=C(Nc1ccc(Nc2ccnc3[nH]c(=O)c4c(c23)CCCC4)cc1)c1cccc(C(F)(F)F)c1F]

2-Fluoro-N-[4-(6-oxo-5,6,7,8,9,10-hexahydrobenzo[c][1,8]naphthyridin-1-ylamino)-phenyl]-3-trifluoromethyl-benzamide (11)

The title compound was synthesized according to the procedure described for the preparation of Example 5. LC-MS (M+H=497, obsd.=497). $^1$H NMR (400 MHz, d6-DMSO): δ 1.67 (m, 2H), 1.73 (m, 2H), 2.53 (m, 2H), 3.20 (m, 2H), 6.77 (m, 1H), 7.28 (m, 2H), 7.56 (m, 1H), 7.76 (m, 2H), 7.92-8.06 (m, 3H), 8.48 (s, 1H), 10.70 (s, 1H).

Example 12

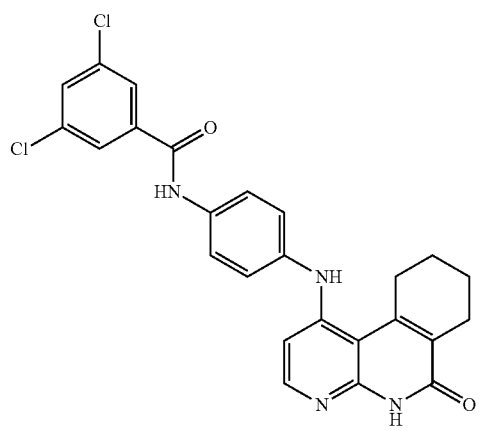 [SMILES: O=C(Nc1ccc(Nc2ccnc3[nH]c(=O)c4c(c23)CCCC4)cc1)c1cc(Cl)cc(Cl)c1]

3,5-Dichloro-N-[4-(6-oxo-5,6,7,8,9,10-hexahydrobenzo[c][1,8]naphthyridin-1-ylamino)-phenyl]-1-benzamide (12)

The title compound was synthesized according to the procedure described for the preparation of Example 5. LC-MS (M+H=479, obsd.=479). $^1$H NMR (400 MHz, d6-DMSO): δ 1.67 (m, 2H), 1.73 (m, 2H), 2.53 (m, 2H), 3.20 (m, 2H), 6.78 (m, 1H), 7.27 (m, 1H), 7.78 (m, 2H), 7.89 (s, 1H), 7.99 (m, 2H), 8.05 (m, 1H), 10.48 (s, 1H).

Example 13

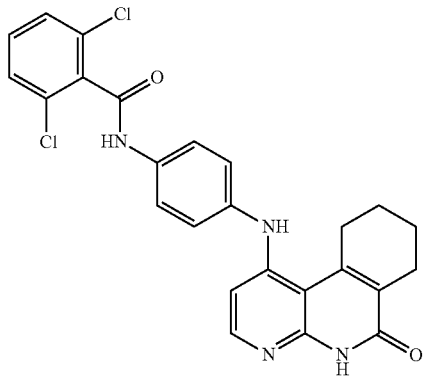 [SMILES: O=C(Nc1ccc(Nc2ccnc3[nH]c(=O)c4c(c23)CCCC4)cc1)c1c(Cl)cccc1Cl]

2,6-Dichloro-N-[4-(6-oxo-5,6,7,8,9,10-hexahydrobenzo[c][1,8]naphthyridin-1-ylamino)-phenyl]-1-benzamide (13)

The title compound was synthesized according to the procedure described for the preparation of Example 5. LC-MS (M+H=479, obsd.=479). $^1$H NMR (400 MHz, d6-DMSO): δ 1.66 (m, 2H), 1.71 (m, 2H), 2.53 (m, 2H), 3.16 (m, 2H), 6.82 (m, 1H), 7.24 (m, 2H), 7.53 (m, 1H), 7.58 (m, 2H), 7.68 (m, 2H), 8.05 (m, 1H), 10.74 (s, 1H).

Example 14

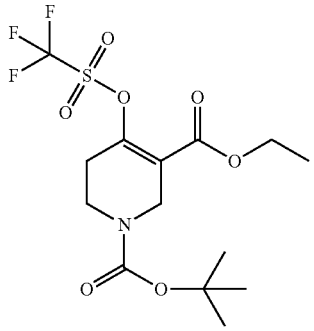 [SMILES: CCOC(=O)C1=C(OS(=O)(=O)C(F)(F)F)CCN(C(=O)OC(C)(C)C)C1]

4-Trifluoromethanesulfonyloxy-5,6-dihydro-2H-pyridine-1,3-dicarboxylic acid 1-tert-butyl ester 3-ethyl ester (14)

The title compound was synthesized according to the procedure described for the preparation of Example 1.

Example 15

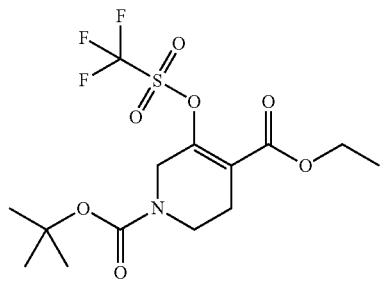 [SMILES: CCOC(=O)C1=C(OS(=O)(=O)C(F)(F)F)CN(C(=O)OC(C)(C)C)CC1]

5-Trifluoromethanesulfonyloxy-3,6-dihydro-2H-pyridine-1,4-dicarboxylic acid 1-tert-butyl ester 4-ethyl ester (15)

The title compound was synthesized according to the procedure described for the preparation of Example 1.

Example 16

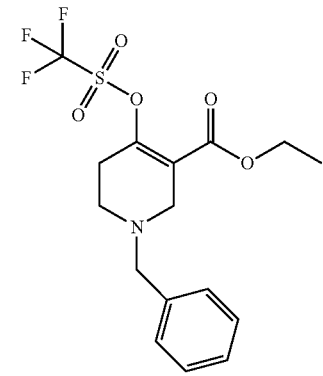 [SMILES: CCOC(=O)C1=C(OS(=O)(=O)C(F)(F)F)CCN(Cc2ccccc2)C1]

1-Benzyl-4-trifluoromethanesulfonyloxy-1,2,5,6-tetrahydro-pyridine-3-carboxylic acid ethyl ester (16)

The title compound was synthesized according to the procedure described for the preparation of Example 1.

Example 17

1-Benzyl-5-trifluoromethanesulfonyloxy-1,2,3,6-tetrahydro-pyridine-4-carboxylic acid ethyl ester (17)

The title compound was synthesized according to the procedure described for the preparation of Example 1.

Example 18

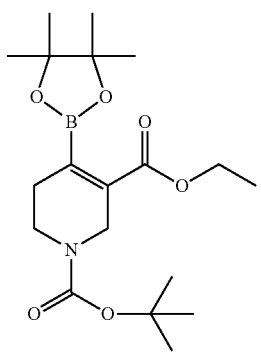 [SMILES: CCOC(=O)C1=C(B2OC(C)(C)C(C)(C)O2)CCN(C(=O)OC(C)(C)C)C1]

4-(4,4,5,5-Tetramethyl-[1,3]dioxaborolan-2-yl)-5,6-dihydro-2H-pyridine-1,3-dicarboxylic acod 1-tert-butyl ester 3-ethyl ester (18)

The title compound was synthesized according to the procedure described for the preparation of Example 2. LC-MS (M+H=382, obsd.=382). $^1$H NMR (400 MHz, d6-DMSO): δ 1.22 (t, 3H), 1.24 (s, 12H), 1.44 (s, 9H), 2.33 m, 2H), 3.45 (m, 2H), 4.10 (m, 2H), 4.21 (q, 2H).

Example 19

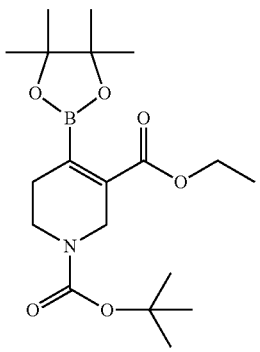

5-(4,4,5,5-Tetramethyl-[1,3,2]dioxaborolan-2-yl)-3,6-dihydro-2H-pyridine-1,4-dicarboxylic acid 1-tert-butyl ester 4-ethyl ester (19)

The title compound was synthesized according to the procedure described for the preparation of Example 2. LC-MS (M+H=382, obsd.=382). $^1$H NMR (400 MHz, d6-DMSO): δ 1.22 (t, 3H), 1.24 (s, 12H), 1.44 (s, 9H), 2.33 m, 2H), 3.45 (m, 2H), 4.10 (m, 2H), 4.21 (q, 2H).

Example 20

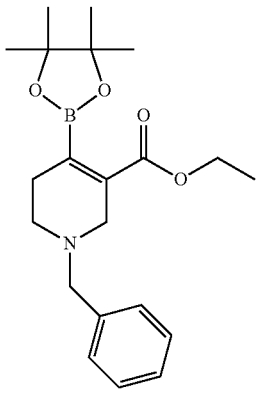 [SMILES: CCOC(=O)C1=C(B2OC(C)(C)C(C)(C)O2)CCN(Cc2ccccc2)C1]

1-Benzyl-4-(4,4,5,5-tetramethyl-[1,3,2]dioxaborolan-2-yl)-1,2,5,6-tetrahydro-pyridine-3-carboxylic acid ethyl ester (20)

The title compound was synthesized according to the procedure described for the preparation of Example 2. LC-MS (M+H=372, obsd.=372). $^1$H NMR (400 MHz, d6-DMSO): δ 1.22 (t, 3H), 1.32 (s, 12H), 2.34 (m, 1H), 2.50 (m, 1H), 3.21 (m, 2H), 3.62 (m, 2H), 3.62 (s, 2H), 4.17 (q, 2H), 7.33 (m, 5H).

Example 21

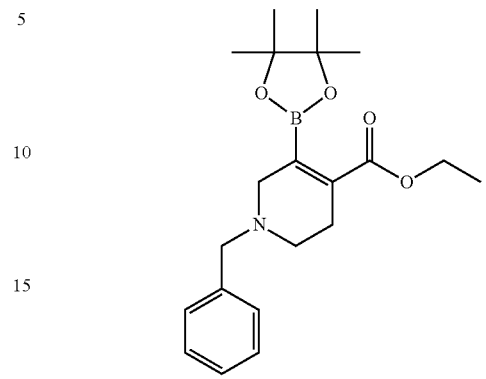

1-Benzyl-5-(4,4,5,5-tetramethyl-[1,3,2]dioxaborolan-2-yl)-1,2,3,6-tetrahydro-pyridine-4-carboxylic acid ethyl ester (21)

The title compound was synthesized according to the procedure described for the preparation of Example 2. LC-MS (M+H=372, obsd.=372). $^1$H NMR (400 MHz, d6-DMSO): δ 1.25 (t, 3H), 1.32 (s, 12H), 2.42 (m, 2H), 2.61 (m, 2H), 3.14 (s, 2H), 3.62 (s, 2H), 4.17 (q, 2H), 7.33 (m, 5H).

Example 22

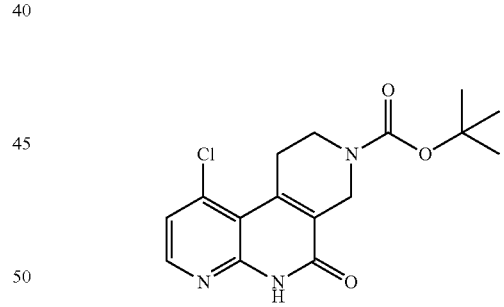

4-Chloro-9-oxo-5,8,9,10-tetrahydro-6H-1,7,10-tri-aza-phenanthrene-7-carboxylic acid tert-butyl ester (22)

The title compound was synthesized according to the procedure described for the preparation of Example 3. LC-MS (M+H=336, obsd.=336). $^1$H NMR (400 MHz, d6-DMSO): δ 1.44 (s, 9H), 3.29 (m, 2H), 3.50 (m, 2H), 4.28 (s, 2H) 7.36 (d, 1H), 8.38 (d, 1H).

Example 23

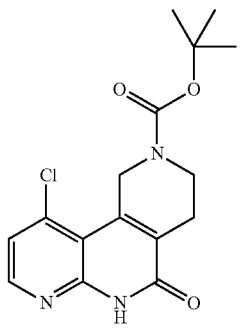 [SMILES: CC(C)(C)OC(=O)N1CCc2c(c3c(Cl)ccnc3[nH]c2=O)C1]

4-Chloro-9-oxo-7,8,9,10-tetrahydro-5H-1,6,10-tri-aza-phenanthrene-6-carboxylic acid tert-butyl ester (23)

The title compound was synthesized according to the procedure described for the preparation of Example 3. LC-MS (M+H=336, obsd.=336). $^1$H NMR (400 MHz, d6-DMSO): δ 1.43 (s, 9H), 3.39 (m, 2H), 3.68 (m, 2H), 4.98 (s, 2H) 7.38 (d, 1H), 8.35 (d, 1H).

Example 24

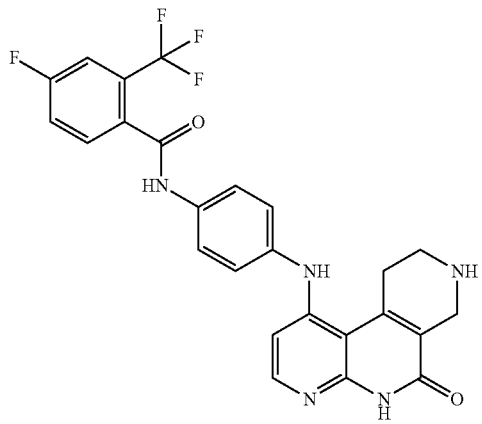 [SMILES: O=C(Nc1ccc(Nc2ccnc3[nH]c(=O)c4c(c23)CCNC4)cc1)c1ccc(F)cc1C(F)(F)F]

4-Fluoro-N-[4-(9-oxo-5,6,7,8,9,10-hexahydro-1,7,10-triaza-phenanthren-4-ylamino)-phenyl]-2-trifluoromethyl-benzamide (24)

The title compound was synthesized according to the procedure described for the preparation of Example 5. LC-MS (M+H=498, obsd.=498). $^1$H NMR (400 MHz, d6-DMSO): δ 3.31 (m, 2H), 3.47 (m, 2H), 4.04 (s, 2H), 6.79 (m, 1H), 6.99 (m, 2H), 7.68 (m, 2H), 7.80 (m, 2H), 8.14 (m, 1H), 8.31 (s, 1H), 9.14 (br, 2H), 10.59 (s, 1H).

Example 25

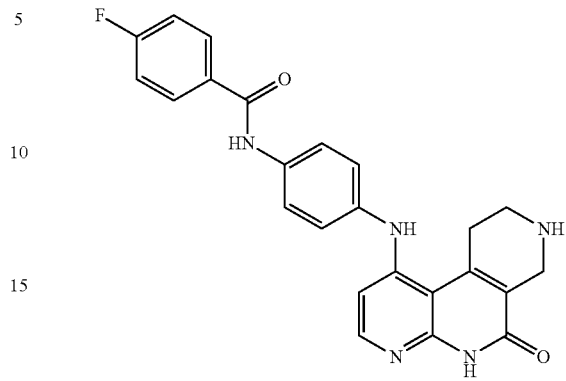

4-Fluoro-N-[4-(9-oxo-5,6,7,8,9,10-hexahydro-1,7,10-triaza-phenanthren-4-ylamino)-phenyl]-benzamide (25)

The title compound was synthesized according to the procedure described for the preparation of Example 5. LC-MS (M+H=430, obsd.=430). $^1$H NMR (400 MHz, d6-DMSO): δ 3.31 (m, 2H), 3.47 (m, 2H), 4.04 (s, 2H), 6.80 (m, 1H), 7.19 (m, 3H), 7.37 (m, 3H), 7.78 (m, 2H), 8.05 (m, 2H), 8.14 (m, 1H), 8.21 (s, 1H), 9.18 (br, 2H), 10.59 (s, 1H).

Example 26

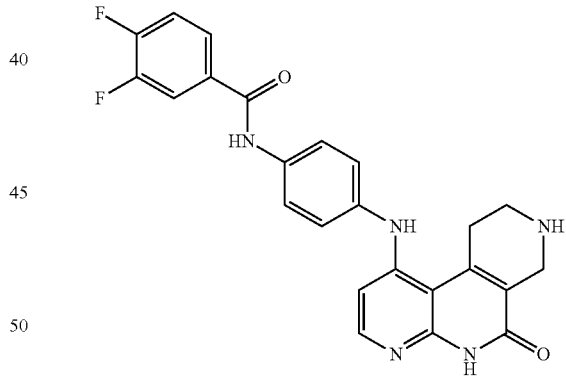

3,4-Difluoro-N-[4-(9-oxo-5,6,7,8,9,10-hexahydro-1,7,10-triaza-phenanthren-4-ylamino)-phenyl]-benzamide (26)

The title compound was synthesized according to the procedure described for the preparation of Example 5. LC-MS (M+H=448, obsd.=448). $^1$H NMR (400 MHz, d6-DMSO): δ 3.30 (m, 2H), 3.49 (m, 2H), 4.04 (s, 2H), 6.79 (d, 1H), 7.19 (d, 2H), 7.77 (m, 4H), 8.14 (m, 1H), 8.24 (s, 1H), 9.04 (br, 2H), 10.34 (s, 1H).

Example 27

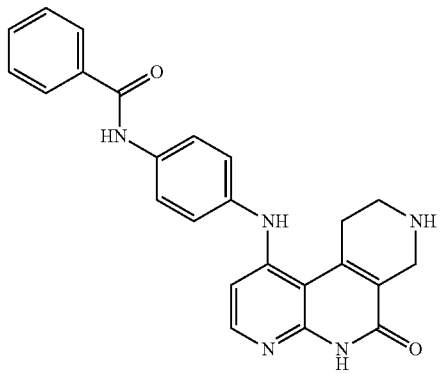 [SMILES: O=C(Nc1ccc(Nc2ccnc3[nH]c(=O)c4c(c23)CCNC4)cc1)c1ccccc1]

N-[4-(9-oxo-5,6,7,8,9,10-hexahydro-1,7,10-triaza-phenanthren-4-ylamino)-phenyl]-benzamide (27)

The title compound was synthesized according to the procedure described for the preparation of Example 5. LC-MS (M+H=412, obsd.=412). $^1$H NMR (400 MHz, d6-DMSO): δ 3.31 (m, 2H), 3.46 (m, 2H), 4.14 (s, 2H), 6.79 (d, 1H), 7.19 (d, 2H), 7.56 (m, 4H), 7.78 (d, 2H), 7.95 (d, 2H), 8.15 (d, 1H), 9.06 (br, 2H), 10.28 (s, 1H).

Example 28

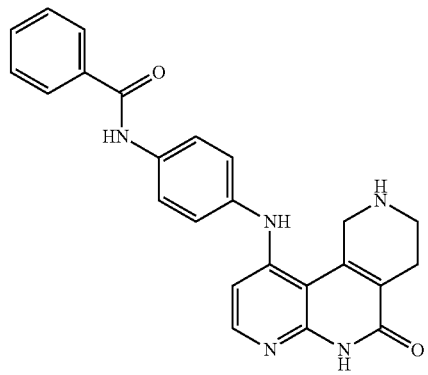 [SMILES: O=C(Nc1ccc(Nc2ccnc3[nH]c(=O)c4c(c23)CNCC4)cc1)c1ccccc1]

N-[4-(9-oxo-5,6,7,8,9,10-hexahydro-1,6,10-triaza-phenanthren-4-ylamino)-phenyl]-benzamide (28)

The title compound was synthesized according to the procedure described for the preparation of Example 5. LC-MS (M+H=412, obsd.=412). $^1$H NMR (400 MHz, d6-DMSO): δ 3.35 (m, 2H), 3.65 (m, 2H), 4.12 (s, 2H), 6.99 (d, 1H), 7.20 (d, 2H), 7.57 (m, 4H), 7.77 (d, 2H), 7.80 (d, 2H), 8.12 (d, 1H), 9.01 (br, 2H), 10.16 (s, 1H).

Example 29

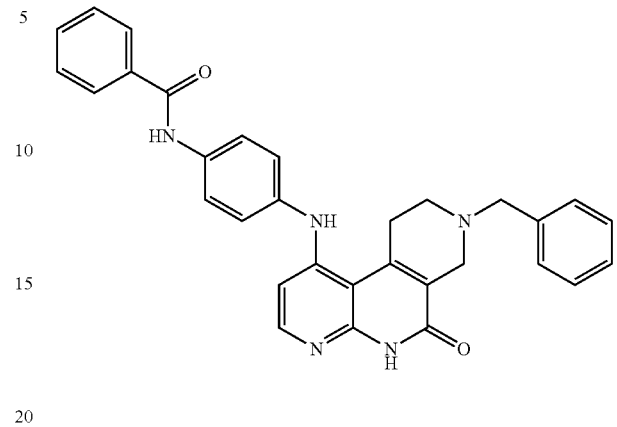

N-[4-(7-Benzyl-9-oxo-5,6,7,8,9,10-hexahydro-1,7,10-triaza-phenanthren-4-ylamino)-phenyl]-benzamide (29)

The title compound was synthesized according to the procedure described for the preparation of Example 5. LC-MS (M+H=502, obsd.=502). $^1$H NMR (400 MHz, d6-DMSO): δ 3.27 (m, 2H), 3.57 (m, 2H), 4.14 (m, 2H), 4.53 (s, 2H), 6.79 (d, 1H), 7.17 (d, 2H), 7.59 (m, 7H), 7.79 (d, 2H), 7.96 (d, 2H), 8.15 (d, 1H), 8.21 (s, 1H), 10.29 (s, 1H).

Example 30

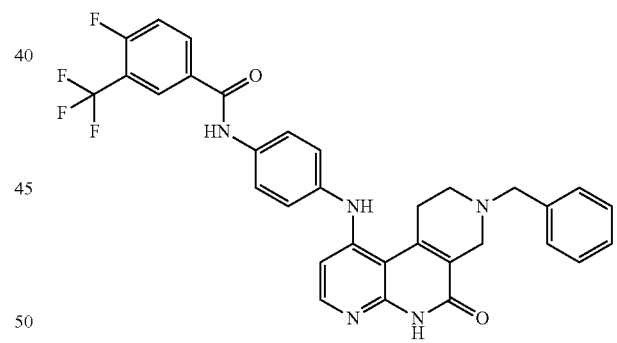

4-Fluoro-N-[4-(7-benzyl-9-oxo-5,6,7,8,9,10-hexahydro-1,7,10-triaza-phenanthren-4-ylamino)-phenyl]-2-trifluoromethyl-benzamide (30)

The title compound was synthesized according to the procedure described for the preparation of Example 5. LC-MS (M+H=588, obsd.=588). $^1$H NMR (400 MHz, d6-DMSO): δ 3.27 (m, 2H), 3.57 (m, 2H), 4.14 (m, 2H), 4.53 (s, 2H), 6.79 (d, 1H), 7.17 (d, 2H), 7.51 (m, 7H), 7.67 (d, 2H), 7.86 (d, 2H), 8.13 (d, 1H), 8.16 (s, 1H), 10.59 (s, 1H).

Example 31

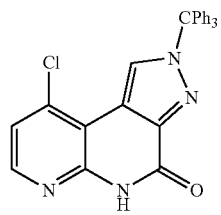

9-Chloro-2-trityl-2H-pyrazolo[3,4-c][1,8]naphthyridin-4(5H)-one (31)

Methyl 4-(4,4,5,5-tetramethyl-1,3,2-dioxaborolan-2-yl)-1-trityl-1H-pyrazole-3-carboxylate (1165 mg, 2.36 mmol), 4-chloro-3-iodopyridin-2-amine (600 mg, 2.36 mmol), Pd(OAc)$_2$ (37 mg, 0.17 mmol) and S-phos (135 mg, 0.33 mmol) was placed in a 20 ml sealed tube. Dioxane (2 mL) and aqueous K$_2$CO$_3$ (1.72 mL, 2.0 M) were added, and the reaction mixture was stirred at 130° C. for 3 h. The reaction mixture was cooled to room temperature, and the precipitate was filtered. The precipitate was washed with EtOAc, water, and methanol to provide 31 (828 mg, 76% yield) as a white solid. LC-MS (M+Na=485, obsd.=485).

Example 32

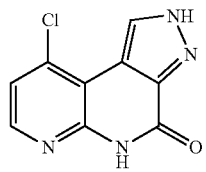 [SMILES: O=c1[nH]c2nccc(Cl)c2c2c[nH]nc12]

9-Chloro-2H-pyrazolo[3,4-c][1,8]naphthyridin-4(5H)-one (32)

To a suspension solution of the compound of Example 31 (800 mg, 1.73 mmol) in acetone (12 mL), was added 4.0 M HCl in dioxane (2.5 mL, 10.37 mmol). The reaction mixture was stirred overnight at 35° C. The resulting precipitate was filtered, and washed with acetone to provide 32 (400 mg, 100% yield) as a yellow product. LC-MS (M+H=221, obsd.=221).

Example 33

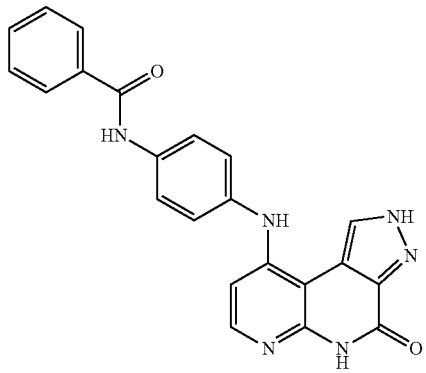 [SMILES: O=C(Nc1ccc(Nc2ccnc3[nH]c(=O)c4n[nH]cc4c23)cc1)c1ccccc1]

N-(4-(4-oxo-4,5-dihydro-2H-pyrazolo[3,4-c][1,8]naphthyridin-9-ylamino)phenyl)benzamide (33)

The compound of Example 31 (80 mg, 0.36 mmol), N-(4-aminophenyl)-benzamide (114 mg, 0.38 mmol), NMP (1 mL), and 4.0 M HCl in dioxane (90 µl, 0.36 mmol) were added to a sealed-tube vessel. The tube was placed in the microwave at 130° C. for 30 minutes. The crude reaction mixture was purified by HPLC to provide 33 (11 mg, 6% yield) as a yellow solid. LC-MS (M+H=397, obsd.=397).

Example 34

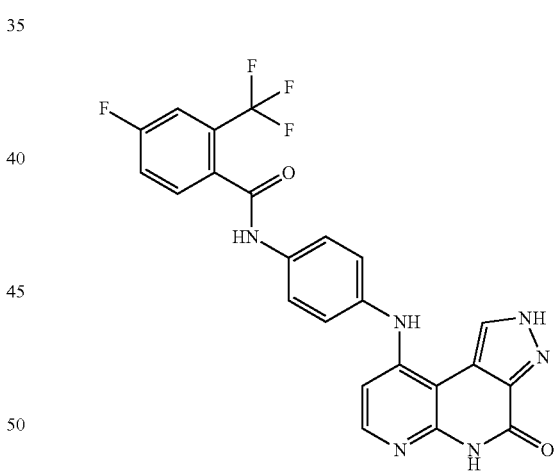

4-fluoro-N-(4-(4-oxo-4,5-dihydro-2H-pyrazolo naphthyridin-9-ylamino) phenyl)-2-(trifluoromethyl) benzamide (34)

The compound of Example 31 (300 mg, 1.36 mmol), N-(4-aminophenyl)-4-fluoro-2-(trifluoromethyl)benzamide (425 mg, 1.43 mmol), and HCl (4.0M in dioxane) (272 µl, 2.72 mmol) were dissolved in NMP (8.0 mL), and stirred at 150° C. for 3 h. The reaction mixture was cooled to room temperature, and poured into aqueous NaHCO$_3$ aq (100 mL). The resulting precipitate was filtered, and dried under vacuum to provide 34 (450 mg) as a brown solid. LC-MS (M+H=483, obsd.=483).

Example 35

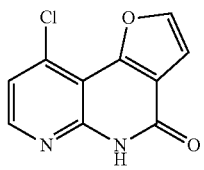 [SMILES: O=c1[nH]c2nccc(Cl)c2c2occc12]

9-Chloro-5H-furo[3,2-c][1,8]naphthyridin-4-one (35)

To a solution of diisopropylamine (2.72 g, 3.77 mL, 26.9 mmol) in THF (50 mL) under argon was added ethyl magnesium chloride (2M solution in THF, 12.8 mL, 25.6 mmol). The solution was stirred at room temperature under argon for 24 h. Ethyl 3-furoate (1.8 g, 1.73 mL, 12.8 mmol) was added slowly and the colored solution was stirred for 15 min at room temperature. Tributyltin chloride (10.8 g, 9.0 mL, 33.3 mmol) was added and the mixture stirred for 2 h at room temperature under argon. The reaction was quenched by addition of sat. NH$_4$Cl solution, diluted with H$_2$O, and extracted twice with CH$_2$Cl$_2$. The combined extracts were dried over Na$_2$SO$_4$ and the solvent removed under reduced pressure. The crude mixture was purified by chromatography on silica (0-10% EtOAc in heptane) to provide the tin intermediate (2.36 g, 43%) as a pale yellow oil. $^1$H NMR (400 MHz, CDCl$_3$) δ ppm 0.89 (t, J=7.30 Hz, 9H) 1.17 (t, J=2.15 Hz, 6H) 1.25-1.35 (m, 6H) 1.36 (t, J=7.13 Hz, 3H) 1.51-1.60 (m, 6H) 4.31 (q, J=7.13 Hz, 2H) 6.74 (d, J=1.71 Hz, 1H) 7.66 (d, J=1.76 Hz, 1H).

2-Amino-4-chloro-3-iodopyridine (1.0 g, 3.93 mmol), the tin intermediate from above (2.02 g, 4.72 mmol) and Pd(Ph$_3$)$_4$ (0.45 g, 0.39 mmol) were suspended in dry dioxane (10 mL), and heated in a microwave (power 200 W, max temperature 150° C.) for 3 hours. The precipitate that formed was collected by filtration and dried to provide 35 (234 mg, 27%) as a white solid. LC-MS (M+H=221, obsd.=221). $^1$H NMR (400 MHz, DMSO-d$_6$) δ ppm 7.17 (d, J=2.00 Hz, 1H) 7.47 (d, J=5.32 Hz, 1H) 8.25 (d, J=2.00 Hz, 1H) 8.45 (d, J=5.27 Hz, 1H) 12.39 (s, 1H).

Example 36

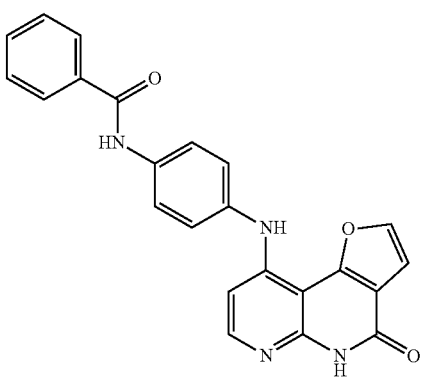 [SMILES: O=C(Nc1ccc(Nc2ccnc3[nH]c(=O)c4ccoc4c23)cc1)c1ccccc1]

N-[4-(4-oxo-4,5-dihydro-furo[3,2-c][1,8]naphthyridin-9-ylamino)-phenyl]-benzamide (36)

9-Chloro-5H-furo[3,2-c][1,8]naphthyridin-4-one (80 mg, 0.36 mmol) and 4'-aminobenzanilide (0.39 g, 1.81 mmol) were combined and heated in a microwave (250 W, 150° C.) for 1 hour. The crude material was absorbed onto Celite and purified by chromatography on silica (0-10% methanol in CH$_2$Cl$_2$) to provide 36 (7 mg, 5%) as a yellow solid. LC-MS (M+H=397, obsd.=397). $^1$H NMR (400 MHz, DMSO-d$_6$) δ ppm 5.16 (s, 1H) 6.61-6.67 (m, 1H) 6.70 (d, J=5.86 Hz, 1H) 7.00-7.05 (m, 1H) 7.12 (d, J=2.00 Hz, 1H) 7.41 (s, 1H) 7.55 (s, 2H) 7.86 (d, J=8.83 Hz, 1H) 7.96 (s, 2H) 8.05-8.11 (m, 1H) 8.12 (d, J=2.00 Hz, 1H) 8.45 (s, 1H) 10.33 (s, 1H) 11.82 (s, 1H).

Example 37

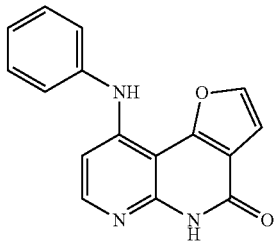 [SMILES: O=c1[nH]c2nccc(Nc3ccccc3)c2c2occc12]

9-Phenylamino-5H-furo[3,2-c][1,8]naphthyridin-4-one (37)

9-Chloro-5H-furo[3,2-c][1,8]naphthyridin-4-one (80 mg, 0.36 mmol), aniline (0.51 mmol), tris(dibenzylideneacetone)dipalladium (17 mg, 0.02 mmol), X-phos (35 mg, 0.07 mmol), and K$_2$CO$_3$ (100 mg, 0.73 mmol) were combined under argon in anhydrous t-butanol (3 mL), and heated to reflux for 16 h. The crude mixture was diluted with CH$_2$Cl$_2$ and MeOH, absorbed onto Celite, and purified by chromatography on silica (0-5% MeOH in CH$_2$Cl$_2$) to provide 37 (20 mg, 20%) as a white solid. LC-MS (M+H=278, obsd.=278). $^1$H NMR (400 MHz, DMSO-d$_6$) δ ppm 6.77 (d, J=5.81 Hz, 1H) 7.12 (d, J=2.05 Hz, 1H) 7.17-7.23 (m, 1H) 7.38-7.47 (m, 4H) 8.10 (d, J=5.81 Hz, 1H) 8.12 (d, J=2.00 Hz, 1H) 8.50 (s, 1H) 11.85 (s, 1H).

Example 38

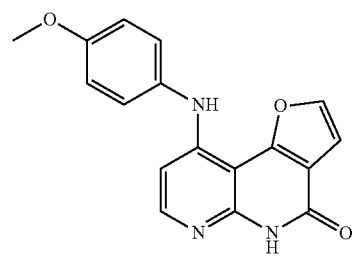 [SMILES: COc1ccc(Nc2ccnc3[nH]c(=O)c4ccoc4c23)cc1]

9-(4-Methoxy-phenylamino)-5H-furo[3,2-c][1,8] naphthyridin-4-one (38)

The title compound was synthesized according to the procedure described for the preparation of Example 37 to provide 38 (18% yield) as a white solid. LC-MS (M+H=308, obsd.=308). ¹H NMR (400 MHz, DMSO-d₆) δ ppm 3.79 (s, 3H) 6.49 (d, J=5.91 Hz, 1H) 7.00-7.05 (m, 2H) 7.11 (d, J=2.05 Hz, 1H) 7.30-7.35 (m, 2H) 8.03 (d, J=5.86 Hz, 1H) 8.10 (d, J=2.05 Hz, 1H) 8.33 (s, 1H) 11.79 (s, 1H).

Example 39

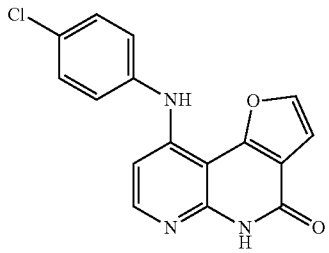 [SMILES: O=c1[nH]c2nccc(Nc3ccc(Cl)cc3)c2c2occc12]

9-(4-Chloro-phenylamino)-5H-furo[3,2-c][1,8]naph-thyridin-4-one (39)

The title compound was synthesized according to the procedure described for the preparation of Example 37 to provide 39 (12% yield) as a white solid. LC-MS (M+H=312, obsd.=312). ¹H NMR (400 MHz, DMSO-d₆) δ ppm 6.79 (d, J=5.81 Hz, 1H) 7.12 (d, J=2.00 Hz, 1H) 7.42 (d, J=6.64 Hz, 2H) 7.45-7.50 (m, 2H) 8.13 (d, J=1.90 Hz, 2H) 8.59 (s, 1H) 11.87 (br. s., 1H).

Example 40

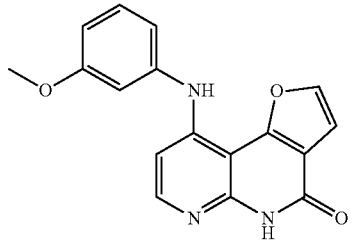 [SMILES: COc1cccc(Nc2ccnc3[nH]c(=O)c4ccoc4c23)c1]

9-(3-Methoxy-phenylamino)-5H-furo[3,2-c][1,8] naphthyridin-4-one (40)

The title compound was synthesized according to the procedure described for the preparation of Example 37 to provide 40 (28% yield) as a white solid. LC-MS (M+H=308, obsd.=308). ¹H NMR (400 MHz, DMSO-d₆) δ ppm 3.77 (s, 3H) 6.73-6.80 (m, 1H) 6.85 (d, J=5.86 Hz, 1H) 6.99 (d, J=1.46 Hz, 2H) 7.12 (d, J=2.00 Hz, 1H) 7.29-7.37 (m, 1H) 8.11 (d, J=5.81 Hz, 1H) 8.13 (d, J=2.05 Hz, 1H) 8.48 (s, 1H) 11.85 (s, 1H).

Example 41

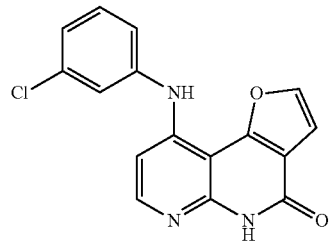 [SMILES: O=c1[nH]c2nccc(Nc3cccc(Cl)c3)c2c2occc12]

9-(3-Chloro-phenylamino)-5H-furo[3,2-c][1,8]naph-thyridin-4-one (41)

The title compound was synthesized according to the procedure described for the preparation of Example 37 to provide 41 (18% yield) as a white solid. LC-MS (M+H=312, obsd.=312). ¹H NMR (400 MHz, DMSO-d₆) δ ppm 6.88 (d, J=5.81 Hz, 1H) 7.12 (d, J=2.00 Hz, 1H) 7.20 (ddd, J=7.78, 1.95, 1.10 Hz, 1H) 7.38 (d, J=1.85 Hz, 1H) 7.42 (d, J=7.86 Hz, 1H) 7.47 (t, J=1.98 Hz, 1H) 8.13 (d, J=2.00 Hz, 1H) 8.16 (d, J=5.81 Hz, 1H) 8.66 (s, 1H) 11.90 (s, 1H).

Example 42

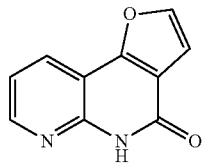 [SMILES: O=c1[nH]c2ncccc2c2occc12]

5H-Furo[3,2-c][1,8]naphthyridin-4-one (42)

3-Furoic acid (2.5 g, 22.3 mmol), thionyl chloride (7.22 ml, 0.0992 mole) and toluene were combined and heated to 70° C. for 2.5 h. The mixture was concentrated, and then resuspended in CH₂Cl₂ (44 mL) and cooled to 0° C. 2-Amino-3-bromopyridine (5.13 g, 29.6 mmol) and triethylamine (3.07 g, 30.3 mmol) were added, and the mixture was stirred overnight at room temperature. The reaction was quenched with 5% HCl (40 mL), and the product was extracted with EtOAc. The organic extracts were dried over MgSO₄, filtered, and concentrated under reduced pressure. The crude product was purified by silica gel chromatography eluting with heptane/EtOAc (7/3) to provide furan-3-carboxylic acid (3-bromo-pyridin-2-yl)-(furan-3-carbonyl) amide (1.14 g) as a yellow solid.

Furan-3-carboxylic acid (3-bromo-pyridin-2-yl)-(furan-3-carbonyl) amide (180 mg, 0.50 mmol), tristriphenylphosphinepalladium (58 mg, 0.05 mmol), potassium acetate (75 mg, 0.77 mmol) and dimethylacetamide (4 mL) were combined in a 10 ml Microwave tube and heated at 140° C. and 300 W for 30 minutes. The mixture was poured into 1:1 brine:water (15 mL) and extracted with ether (3×10 mL). The organic extracts were dried over sodium sulfate, filtered, and concentrated under reduced pressure. The crude product was purified by silica gel chromatography eluting with heptane:EtOAc (1:1) to provide 42. ¹H NMR (400 MHz, DMSO-d₆) δ ppm 7.11 (d) 7.34 (dd) 8.16 (d) 8.33 (s) 8.55 (dd) 12.12 (br. s.)

Example 43

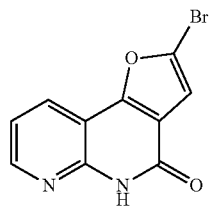 [SMILES: O=c1[nH]c2ncccc2c2oc(Br)cc12]

2-Bromo-5H-furo[3,2-c][1,8]naphthyridin-4-one (43)

5H-Furo[3,2-c][1,8]naphthyridin-4-one (167 mg, 0.897 mmol), NBS (160 mg, 0.897 mmol) and DMF (2.6 ml) were combined and heated at 60° C. for 1.5 h. The reaction mixture was poured into H₂O (20 ml). The resulting precipitate was filtered, and washed with H₂O, and dried under vacuum to provide 43 (183 mg, 77% yield). ¹H NMR (400 MHz, DMSO-d₆) δ ppm 7.28 (s) 7.34 (dd) 8.33 (dt) 8.56 (dd) 12.25 (s).

Example 44

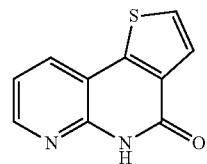 [SMILES: O=c1[nH]c2ncccc2c2sccc12]

5H-Thieno[3,2-c][1,8]naphthyridin-4-one (44)

2-Amino-3-bromopyridine (25 g, 14.4 mmol) and acetic anhydride were combined, and stirred at 125° C. for 12 h, and then at room temperature overnight. The mixture was concentrated, and the residue was redissolved in ether (300 mL), and extracted with 2N NaOH (5×100 mL). The pH of the aqueous extracts was adjusted to pH=7 with concentrated HCl, and the product was extracted with CH₂Cl₂ (5×100 mL). The organic extracts were dried over MgSO₄, filtered, and concentrated to provide N-(3-bromo-pyridin-2-yl)acetamide (72% yield) as an off white solid in. ¹H NMR (400 MHz, CDCl₃) δ ppm 2.44 (s) 6.95 (dd) 7.87 (dd) 7.96 (br. s.) 8.34 (dd). Sodium hydride (60%, 2.96 g, 0.0741 mol) was added portionwise under nitrogen to a solution of N-(3-Bromo-pyridin-2-yl)acetamide (12.25 g, 0.057 mol) in THF (100 mL). When hydrogen evolution ceased, thiophene-3-carbonyl chloride (10.9 g, 0.0741 moles) in THF (25 ml) was added dropwise, and the reaction mixture was stirred overnight at room temperature. The reaction was quenched with H₂O (100 mL), and extracted with CH₂Cl₂ (2×100 ml). The organic extracts were dried over MgSO₄, filtered and concentrated. The crude product was purified by silica gel chromatography eluting with heptane:EtOAc (7:3) to provide thiophene-3-carboxylic acid acetyl-(3-bromo-pyridine-2-yl)-amide (13.4 g, 72% yield) as a white solid. ¹H NMR (400 MHz, CDCl₃-d) d ppm 2.59 (s) 7.14-7.20 (m) 7.20-7.25 (m) 7.67 (dd) 7.95 (dd) 8.46 (dd). LC/MS (M+1) 325.

Thiophene-3-carboxylic acid acetyl-(3-bromo-pyridine-2-yl)-amide (1.05 g, 3.22 mmol) mmol), tristriphenylphosphinepalladium (0.373 g, 0.32 mmol), potassium acetate (0.48 g, 4.84 mmol) and dimethylacetamide (32 mL) were combined and heated at 100° C. for 12 h, then at room temperature over the weekend. The mixture was poured into 1:1 brine:H₂O (50 mL) and extracted with ether (4×25 mL). The organic portion was dried over MgSO₄, filtered and concentrated under reduced pressure. Triturated with MeOH, and then hot acetonitrile to give pure 44. ¹H NMR (400 MHz, DMSO-d₆) δ ppm 7.30 (dd) 7.62 (d) 7.87 (d) 8.32 (dd) 8.51 (dd) 12.11 (br. s.).

Example 45

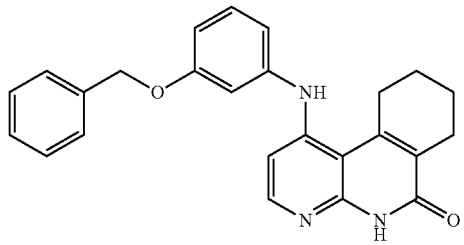 [SMILES: O=c1[nH]c2nccc(Nc3cccc(OCc4ccccc4)c3)c2c2c1CCCC2]

1-(3-Benzyloxy-phenylamino)-7,8,9,10-tetrahydro-5H-benzo[c][1,8]naphthyridin-6-one (45)

The title compound was synthesized according to the procedure described for the preparation of Example 4 to provide 45 (52% yield) as a tan solid. LC-MS (M+H=398, obsd.=398).

Example 46

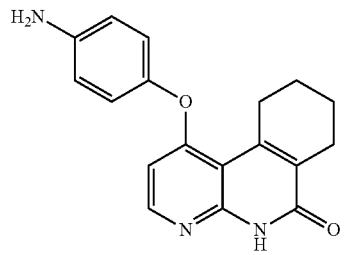 [SMILES: Nc1ccc(Oc2ccnc3[nH]c(=O)c4c(c23)CCCC4)cc1]

1-(4-Amino-phenoxy)-7,8,9,10-tetrahydro-5H-benzo[c][1,8]naphthyridin-6-one (46)

The compound of Example 3 (500 mg, 2.13 mmol), 4-amino phenol (465 mg, 4.26 mmol), and cesium carbonate (2.77 g, 8.52 mmol) were suspended in DMF (20.0 mL), and stirred for 30 minutes at 120° C. in a microwave. The reaction mixture was diluted with H₂O, and the resulting precipitate was filtered. The precipitate was triturated with MeOH, filtered, and dried under vacuum to provide 46 (350 mg, 54% yield) as a tan solid. LC-MS (M+H=308, obsd.=308).

Example 47

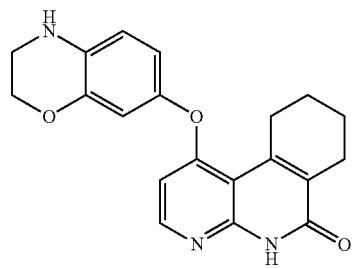 [SMILES: O=c1[nH]c2nccc(Oc3ccc4c(c3)OCCN4)c2c2c1CCCC2]

1-(3,4-Dihydro-2H-benzo[1,4]oxazin-7-yloxy)-7,8,9,10-tetrahydro-5H-benzo[c][1,8]naphthyridin-6-one (47)

The title compound was synthesized according to the procedure described for the preparation of Example 46 to provide 47 (65% yield) as a tan solid. LC-MS (M+H=350, obsd.=350).

Example 48

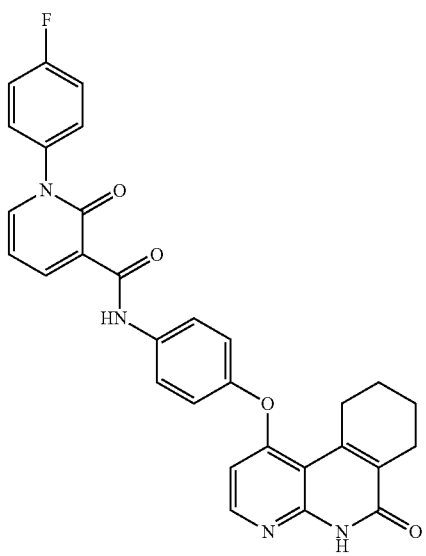 [SMILES: O=C(Nc1ccc(Oc2ccnc3[nH]c(=O)c4c(c23)CCCC4)cc1)c1cccn(-c2ccc(F)cc2)c1=O]

1-(4-Fluoro-phenyl)-2-oxo-1,2-dihydro-pyridine-3-carboxylic acid [4-(6-oxo-5,6,7,8,9,10-hexahydro-benzo[c][1,8]naphthyridin-1-yloxy)-phenyl]-amide (48)

The compound of Example 46 (40 mg, 0.13 mmol), 1-(4-fluoro-phenyl)-2-oxo-1,2-dihydro-pyridine-3-carboxylic acid (45 mg, 0.20 mmol), DIEA (0.06 mL, 0.39 mmol), and Bop-Cl (66 mg, 0.26 mmol) were suspended in dioxane (2.0 mL), and stirred overnight at room temperature. The reaction mixture was diluted with EtOAc/H$_2$O. The resulting precipitate was filtered, washed with H$_2$O, and dried under vacuum to provide 48 (45 mg, 66% yield) as a tan solid. LC-MS (M+H=523, obsd.=523).

Example 49

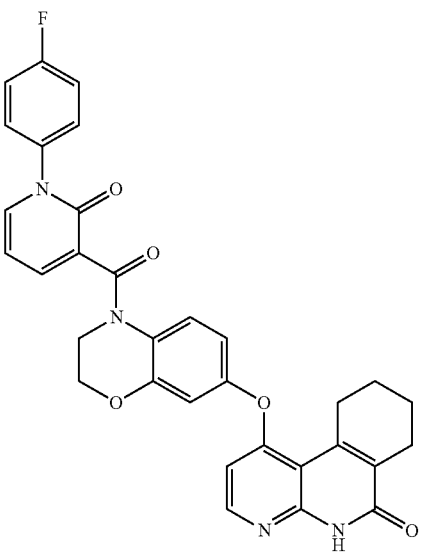 [SMILES: O=C(c1cccn(-c2ccc(F)cc2)c1=O)N1CCOc2cc(Oc3ccnc4[nH]c(=O)c5c(c34)CCCC5)ccc21]

1-{4-[1-(4-Fluoro-phenyl)-2-oxo-1,2-dihydro-pyridine-3-carbonyl]-3,4-dihydro-2H-benzo[1,4]oxazin-7-yloxy}-7,8,9,10-tetrahydro-5H-benzo[c][1,8]naphthyridin-6-one (49)

The title compound was synthesized according to the procedure described for the preparation of Example 48 to provide 49 (51% yield) as a tan solid. LC-MS (M+H=565, obsd.=565).

Example 50

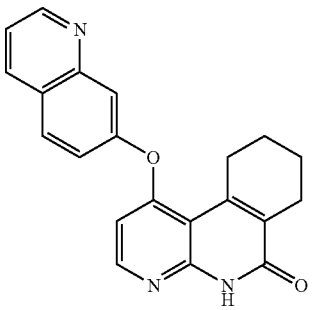 [SMILES: O=c1[nH]c2nccc(Oc3ccc4cccnc4c3)c2c2c1CCCC2]

1-(Quinolin-7-yloxy)-7,8,9,10-tetrahydro-5H-benzo[c][1,8]naphthyridin-6-one (50)

The title compound was synthesized according to the procedure described for the preparation of Example 46 to provide 50 (5% yield) as a tan solid. LC-MS (M+H=344, obsd.=344).

Example 51

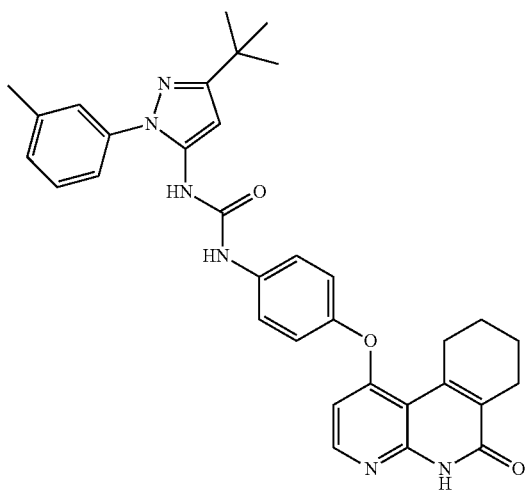 [SMILES: Cc1cccc(-n2nc(C(C)(C)C)cc2NC(=O)Nc2ccc(Oc3ccnc4[nH]c(=O)c5c(c34)CCCC5)cc2)c1]

1-(5-tert-Butyl-2-m-tolyl-2H-pyrazol-3-yl)-3-[4-(6-oxo-5,6,7,8,9,10-hexahydro-benzo[c][1,8]naphthyridin-1-yloxy)-phenyl]-urea (51)

The compound of Example 46 (50 mg, 0.16 mmol), (5-tert-butyl-2-m-tolyl-2H-pyrazol-3-yl)-carbamic acid 2,2,2-trichloro-ethyl ester (79 mg, 0.20 mmol), and DIEA (0.08 mL, 0.49 mmol) were suspended in DMSO (2.0 mL), and stirred overnight at 60° C. The reaction mixture was diluted with EtOAc/H$_2$O, and filtered through an Extrelut column. The column was washed with EtOAc, and the filtrate was concentrated. The crude product was purified via Biotage eluting with a gradient of 25 to 100% EtOAc in hexanes to provide 51 (23 mg, 25% yield) as a tan solid. LC-MS (M+H=563, obsd.=563).

Example 52

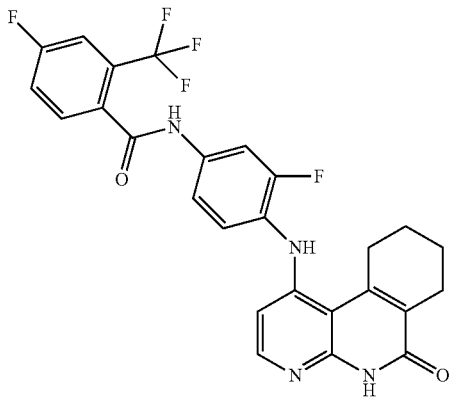 [SMILES: O=C(Nc1ccc(Nc2ccnc3[nH]c(=O)c4c(c23)CCCC4)c(F)c1)c1ccc(F)cc1C(F)(F)F]

4-Fluoro-N-[3-fluoro-4-(6-oxo-5,6,7,8,9,10-hexahydrobenzo[c][1,8]naphthyridin-1-ylamino)-phenyl]-2-trifluoromethyl-benzamide The title compound was synthesized according to the procedure described for the preparation of Example 5. LC-MS (515 (M+H)). $^1$H NMR (400 MHz, d6-DMSO): δ 1.6956 (m, 4H), 2.5071 (m, 2H), 3.2031 (m, 2H), 6.3589 (m, 1H), 7.2997 (m, 2H), 7.7475 (m, 2H), 7.8153 (m, 2H), 8.0407 (m, 1H), 8.6588 (s, 1H), 10.6704 (s, 1H).

Example 53

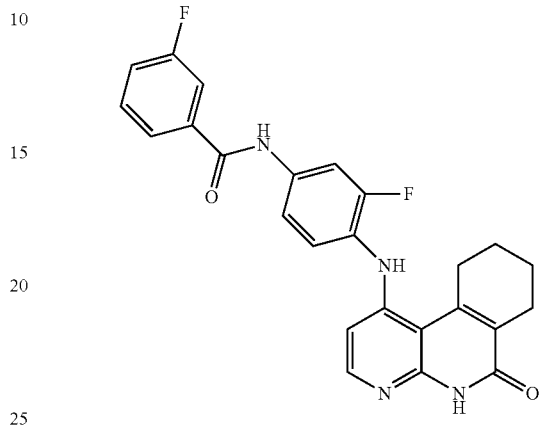

3-Fluoro-N-[3-fluoro-4-(6-oxo-5,6,7,8,9,10-hexahydrobenzo[c][1,8]naphthyridin-1-ylamino)-phenyl]-2-benzamide The title compound was synthesized according to the procedure described for the preparation of Example 5. LC-MS (515 (M+H)). $^1$H NMR (400 MHz, d6-DMSO): δ 1.7002 (m, 4H), 2.5071 (m, 2H), 3.2131 (m, 2H), 6.3989 (m, 1H), 7.2997 (m, 2H), 7.7754 (m, 4H), 7.8153 (m, 2H), 8.0407 (m, 1H), 10.2162 (s, 1H), 10.5404 (s, 1H).

Example 54

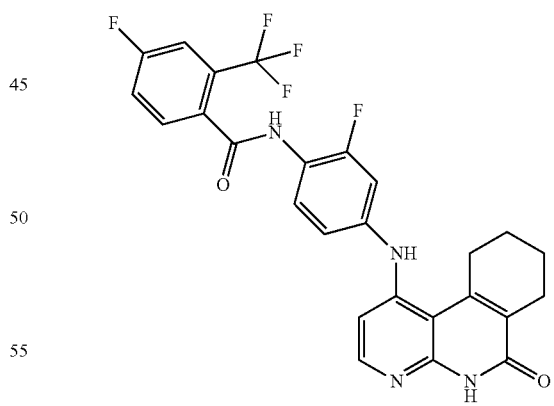

4-Fluoro-N-[2-fluoro-4-(6-oxo-5,6,7,8,9,10-hexahydrobenzo[c][1,8]naphthyridin-1-ylamino)-phenyl]-2-trifluoromethyl-benzamide The title compound was synthesized according to the procedure described for the preparation of Example 5. LC-MS (515 (M+H)). $^1$H NMR (400 MHz, d6-DMSO): δ 1.6389 (m, 2H), 1.7112 (m, 2H), 2.5016 (m, 2H), 3.1131 (m, 2H), 6.9608 (m, 1H), 7.2997 (m, 2H), 7.6834 (m, 2H), 7.7953 (m, 2H), 8.1249 (m, 1H), 8.7188 (s, 1H), 10.3522 (s, 1H).

Example 55

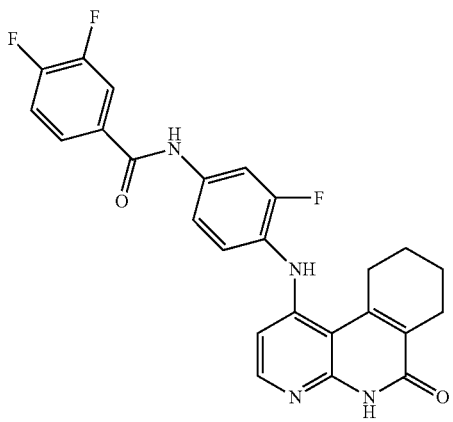 [SMILES: O=C(Nc1ccc(Nc2ccnc3[nH]c(=O)c4c(c23)CCCC4)c(F)c1)c1ccc(F)c(F)c1]

3,4-Difluoro-N-[3-fluoro-4-(6-oxo-5,6,7,8,9,10-hexahydrobenzo[c][1,8]naphthyridin-1-ylamino)-phenyl]-1-benzamide The title compound was synthesized according to the procedure described for the preparation of Example 5. LC-MS (465 (M+H)). $^1$H NMR (400 MHz, d6-DMSO): δ 1.6746 (m, 2H), 1.7378 (m, 2H), 2.5355 (m, 2H), 3.2077 (m, 2H), 7.5552 (m, 1H), 7.6514 (m, 2H), 7.8435 (m, 3H), 8.0607 (m, 2H), 10.2304 (s, 1H), 10.5399 (s, 1H).

Example 56

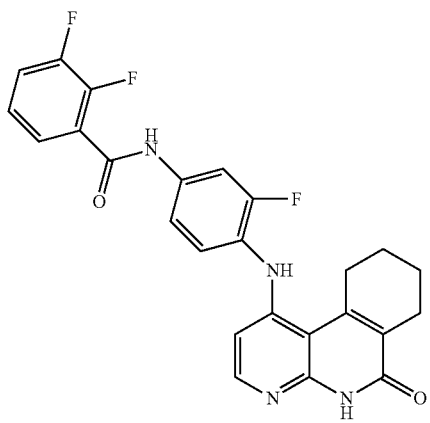 [SMILES: O=C(Nc1ccc(Nc2ccnc3[nH]c(=O)c4c(c23)CCCC4)c(F)c1)c1cccc(F)c1F]

2,3-Difluoro-N-[3-fluoro-4-(6-oxo-5,6,7,8,9,10-hexahydrobenzo[c][1,8]naphthyridin-1-ylamino)-phenyl]-1-benzamide The title compound was synthesized according to the procedure described for the preparation of Example 5. LC-MS (465 (M+H)). $^1$H NMR (400 MHz, d6-DMSO): δ 1.6665 (m, 4H), 2.5355 (m, 2H), 3.1903 (m, 2H), 6.3756 (m, 1H), 7.3327 (m, 2H), 7.4948 (m, 2H), 7.5435 (m, 1H), 7.8061 (m, 1H), 8.0167 (m, 2H), 8.1325 (s, 1H), 10.8161 (s, 1H).

VII. BIOLOGICA DATA

The susceptibility of a particular cell to treatment with the compounds according to the invention was determined by in vitro tests. Typically, a culture of the cell was combined with a compound according to the invention at various concentrations for a period of time that was sufficient to allow the active agents to induce cell death or to inhibit migration, usually between about one hour and one week. In vitro testing was carried out using cultivated cells from a biopsy sample. The viable cells remaining after the treatment then were counted.

Assays

The compounds of Formula I & Formula II described in the examples were tested by the assays given below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

The following Table 2 shows $IC_{50}$ concentrations in nM for compounds of the present invention:

TABLE 2

| Compound Number | Aurora A IC50 (nM) |
| --- | --- |
| 51 | "+" |
| 50 | |
| 49 | "+" |
| 48 | "+" |
| 47 | "+" |
| 46 | "+" |
| 45 | |
| 31 | "+" |
| 34 | "+++" |
| 33 | "++" |
| 32 | |
| 25 | "+" |
| 26 | "++" |
| 27 | "+" |
| 28 | "+" |
| 22 | |
| 23 | |
| 24 | "++" |
| 12 | "++" |
| 13 | "+++" |
| 11 | "+++" |
| 10 | "+++" |
| 9 | "+++" |
| 8 | "+++" |
| 7 | "+++" |
| 30 | "++" |
| 29 | "+" |
| 6 | "+++" |
| 3 | |
| 5 | "++" |
| 36 | "++" |
| 37 | "+" |
| 39 | "+" |
| 40 | "+" |
| 41 | |
| 35 | |
| 38 | "+" |
| 52 | "+++" |
| 53 | "+++" |

TABLE 2-continued

| Compound Number | Aurora A IC50 (nM) |
|---|---|
| 54 | "+++" |
| 55 | "+++" |
| 56 | "+++" | where "+" = 101-1,000 nM
"++" = 11-100 nM
"+++" = 1-10 nM

It is understood in light of the teachings of this invention to one of ordinary skill in the art that certain changes and modifications may be made hereto without departing from the spirit and scope of the invention.

What is claimed is:

1. A compound selected from the group consisting of:
4-Fluoro-N-[4-(6-oxo-5,6,7,8,9,10-hexahydrobenzo[c][1,8]naphthyridin-1-ylamino)-phenyl]-2-trifluoromethyl-1-benzamide;
2,3-Difluoro-N-[4-(6-oxo-5,6,7,8,9,10-hexahydrobenzo[c][1,8]naphthyridin-1-ylamino)-phenyl]-1-benzamide;
3, 4-Difluoro-N-[4-(6-oxo-5,6,7,8,9,10-hexahydrobenzo[c][1,8]naphthyridin-1-ylamino)-phenyl]-1-benzamide;
3, 5-Difluoro-N-[4-(6-oxo-5,6,7,8,9,10-hexahydrobenzo[c][1,8]naphthyridin-1-ylamino)-phenyl]-1-benzamide;
4-Fluoro-N-[4-(6-oxo-5,6,7,8,9,10-hexahydrobenzo[c][1,8]naphthyridin-1-ylamino)-phenyl]-1-benzamide;
2-Fluoro-N-[4-(6-oxo-5,6,7,8,9,10-hexahydrobenzo[c][1,8]naphthyridin-1-ylamino)-phenyl]-3-trifluoromethyl-benzamide;
3, 5-Dichloro-N-[4-(6-oxo-5,6,7,8,9,10-hexahydrobenzo[c][1,8]naphthyridin-1-ylamino)-phenyl]-1-benzamide;
2,6-Dichloro-N-[4-(6-oxo-5,6,7,8,9,10-hexahydrobenzo[c][1,8]naphthyridin-1-ylamino)-phenyl]-1-benzamide;
3-Fluoro-N-[3-fluoro-4-(6-oxo-5,6,7,8,9,10-hexahydrobenzo[c][1,8]naphthyridin-1-ylamino)-phenyl]-2-benzamide;
4-Fluoro-N-[2-fluoro-4-(6-oxo-5,6,7,8,9,10-hexahydrobenzo[c][1,8]naphthyridin-1-ylamino)-phenyl]-2-trifluoromethyl-benzamide;
3, 4-Difluoro-N-[3-fluoro-4-(6-oxo-5,6,7,8,9,10-hexahydrobenzo[c][1,8]naphthyridin-1-ylamino)-phenyl]-1-benzamide; and
2, 3-Difluoro-N-[3-fluoro-4-(6-oxo-5,6,7,8,9,10-hexahydrobenzo[c][1,8]naphthyridin-1-ylamino)-phenyl]-1-benzamide.

2. A pharmaceutical composition comprising a compound of claim 1 or a pharmaceutically acceptable salt, tautomer or stereoisomer thereof, or any mixture thereof, and a pharmaceutically acceptable carrier, excipient, adjuvant and/or diluent.

* * * * *